United States Patent
Lebofsky et al.

(10) Patent No.: US 11,685,947 B2
(45) Date of Patent: *Jun. 27, 2023

(54) DROPLET TAGGING CONTIGUITY PRESERVED TAGMENTED DNA

(71) Applicant: Bio-Rad Laboratories, Inc., Hercules, CA (US)

(72) Inventors: Ronald Lebofsky, Kensington, CA (US); Jeremy Agresti, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 17/236,743

(22) Filed: Apr. 21, 2021

(65) Prior Publication Data

US 2021/0317509 A1     Oct. 14, 2021

Related U.S. Application Data

(62) Division of application No. 15/847,408, filed on Dec. 19, 2017, now Pat. No. 11,021,738.

(Continued)

(51) Int. Cl.
*C12P 19/34*     (2006.01)
*C12Q 1/6809*    (2018.01)
(Continued)

(52) U.S. Cl.
CPC ......... *C12Q 1/6809* (2013.01); *C12Q 1/6869* (2013.01); *G16B 20/00* (2019.02)

(58) Field of Classification Search
CPC ..... C12Q 1/6809; C12Q 1/6869; G16B 20/00
See application file for complete search history.

(56) References Cited

U.S. PATENT DOCUMENTS

| | | |
|---|---|---|
| 2006/0040282 A1 | 2/2006 | Monforte |
| 2010/0120098 A1 | 5/2010 | Grunenwald et al. |

(Continued)

FOREIGN PATENT DOCUMENTS

| | | |
|---|---|---|
| WO | 2012/106546 | 8/2012 |
| WO | 2016/061517 | 4/2016 |
| WO | 2017/151828 A1 | 9/2017 |

OTHER PUBLICATIONS

PCT/US2017/067387, "International Search Report and Written Opinion", dated Apr. 26, 2018, 13 pages.

(Continued)

*Primary Examiner* — Kenneth R Horlick
(74) *Attorney, Agent, or Firm* — Kilpatrick Townsend and Stockton LLP

(57) ABSTRACT

Methods and compositions for maintaining DNA contiguity for sequencing is provided. For example, a plurality of partitions is provided comprising a bead, a forward primer oligonucleotide cleaved from the bead, the forward primer oligonucleotide having a bead-specific barcode and a 3' end specific for and complementary to a first or second adaptor; a reverse primer oligonucleotide having a 3' end complementary to the first or second adaptor, wherein the forward primer 3' end and the reverse primer 3' end are complementary to different adaptors selected from the first adaptor and the second adaptor; and fragments of genomic DNA reacted with an adapter-loaded tagmentase such that the DNA fragments comprise breakpoints in the fragments and an inserted adaptor at the break points, wherein the tagmentase binds the breakpoints to form linked DNA segments in the form of DNA segment-first adaptor tagmentase second adaptor-(DNA segment-first adaptor tagmentase second adaptor) n-DNA segment, where n is any integer and "-" indicates a covalent linkage.

16 Claims, 32 Drawing Sheets

Specification includes a Sequence Listing.

Related U.S. Application Data

(60) Provisional application No. 62/436,288, filed on Dec. 19, 2016.

(51) Int. Cl.
*G16B 20/00* (2019.01)
*C12Q 1/6869* (2018.01)

(56) References Cited

U.S. PATENT DOCUMENTS

| | | |
|---|---|---|
| 2015/0045257 A1 | 2/2015 | Kavanagh et al. |
| 2015/0211054 A1 | 7/2015 | Kostem |
| 2015/0363550 A1 | 12/2015 | Green, Jr. et al. |
| 2015/0368638 A1 | 12/2015 | Steemers |
| 2019/0040382 A1 | 2/2019 | Steemers |
| 2019/0078150 A1 | 3/2019 | Chen |

OTHER PUBLICATIONS

Amini et al., "Haplotype-resolved whole-genome sequencing by contiguity-preserving transposition and combinatorial indexing", Nature Genetics, vol. 46, No. 12, Dec. 2014, pp. 1343-1349.

Amini et al., Correction Notice "Haplotype-resolved whole-genome sequencing by contiguity-preserving transposition and combinatorial indexing", Nature Genetics, May 20, 2015, 15 pgs.

Extended European Search Report in EP Application 17884669.7 dated Jul. 10, 2020; 8 pages.

Snyder, M.W. et al.; "Haplotype-resolved genome sequencing: experimental methods and applications"; Nature Reviews Genetics; vol. 16, No. 6; Jun. 15, 2015; pp. 344-358.

Zheng, G.X.Y. et al.; "Haplotyping germline and cancer genomes with high-throughput linked-read sequencing"; Nature Biotechnology; vol. 34, No. 3; Feb. 1, 2016; pp. 303-311.

6. Split into 96 for block 3 template oligos (96)

...CGCAGAGTAC[0-5]HHHHHHTAGCCATCGCATTGCHHHHHHTACCTCTGAGCTGAA
                                         ATGGAGACTCGACTTHHHHHHATGCHHHHHHHAGCAGCCGTCGCAG
                                                                              ↑
                                                           BC Block 3 template, no UMI,
                                                           NEXTERA Tn5P5 side
                                                           adapter seq 7. Primer extension, wash, pool.

...CGCAGAGTAC[0-5]HHHHHHTAGCCATCGCATTGCHHHHHHTACCTCTGAGCTGAAHHHHHHTCGTCGGCAGCGTC
                  ATGGAGACTCGACTTHHHHHHAGCHHHHHHHAGCAGCCGTCGCAG

NEXTERA Tn5 P5 side adapter seq

8. BC oligo on bead after synthesis
 - after cleavage 105-110 nt

3-AGCAGCCGTCGCAG
                                                                           ↑
                                                                   Block 3 QC probe (we
                                                                   currently don't have)

Custom seq primer
                     ↓
Bead-TTTTTTTTTTTCTACACGACGCTGTTCCGGATCAAGCAGAGTGTATCAAGCAGAGTAC[0-5]HHHHHHTACCATCCATTGCHHHHHHTACCACTGAGCTGAAHHHHHHTCGTCGGCAGCGTC
                                                                                                                    }
                                                                                                                 62-67 nt

FIG. 4

N50x primer (PCR) reminder from previous

AATGATACGGCGACCACCGAGATCTACAC[i5]TCGTCGGCAGCGTC

*Proposal for CPT seq in drops: Swap N50X primer (PCR) with gel bead oligos*

Option 1:

N50x primer (PCR)

P5 grafting — AATGATACGGCGACCACCGAGATCTACAC [bead barcode] NEXTERA ADAPTER specific TCGTCGGCAGCGTC Option 2:

N50x primer (PCR)

P5 grafting-Universal seq (here TruSeqRD1) [bead barcode] NEXTERA ADAPTER specific AATGATACGGCGACCACCGAGATCTACACACACTCTTTCCCTACACGACGCTCTTCCGATCT[beadbarcode]TCGTCGGCAGCGTC

*FIG. 6*

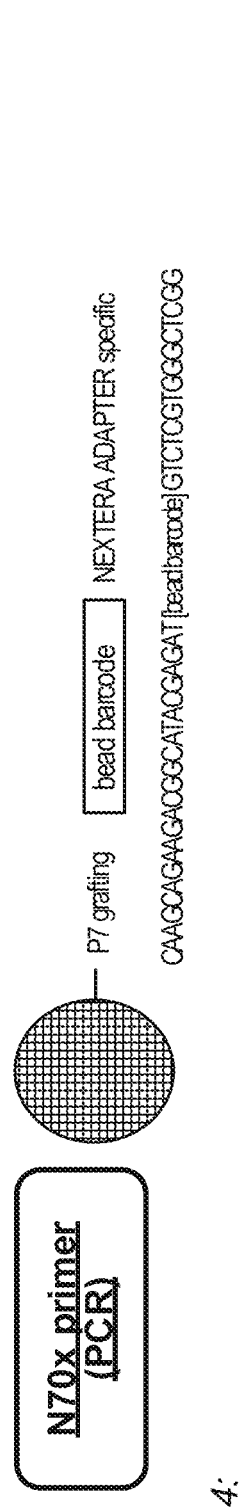
FIG. 7

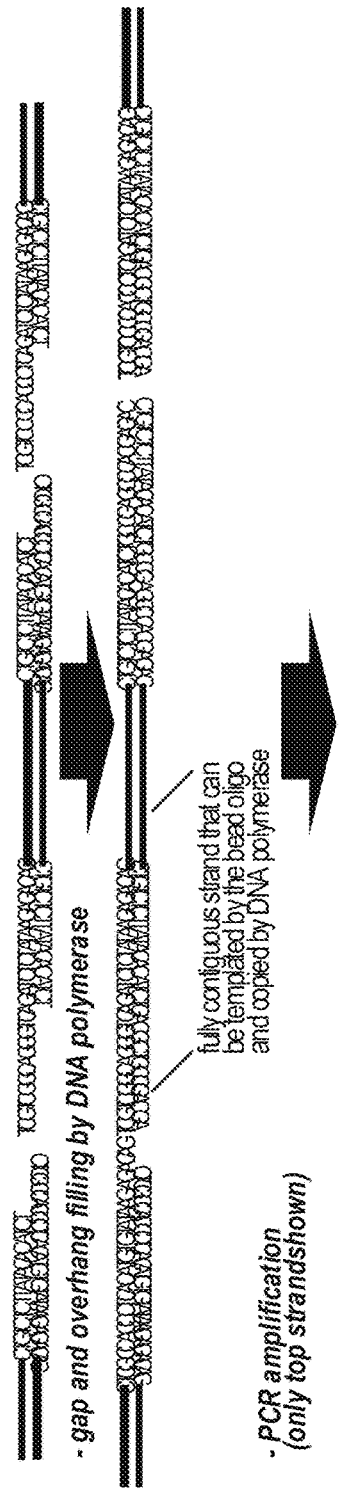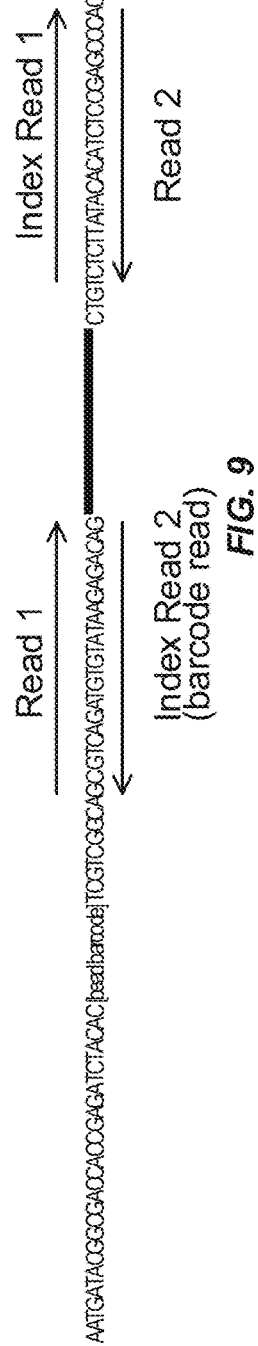
FIG. 9

Additional Primer definitions: for homoadapter Tn5 chemistry

Canonical

N70x primer PCR

P7 grafting – INDEX-NEXTERA ADAPTER specific
CAAGCAGAAGACGGCATACGAGAT [i7] GTCTCGTGGGCTCGG N50x primer PCR P5 grafting – INDEX-NEXTERA ADAPTER specific
AATGATACGGCGACCACCGAGATCTACAC [i5] TCGTCGGCAGCGTC

Modified

N70x primer-TruseqRD2 (PCR)

P7 grafting – INDEX-Universal seq (here TruSeqRD2) NEXTERA ADAPTER specific
CAAGCAGAAGACGGCATACGAGAT [i7] GTGACTGGAGTTCAGACGTGTCTCTTCCGATCTCGTCGGCAGCGTC N50x primer-TruseqRD2 (PCR)

P5 grafting – INDEX-Universal seq (here TruSeqRD1) NEXTERA ADAPTER specific
AATGATACGGCGACCACCGAGATCTACAC [i5] ACACTCTTTCCCTACACGACGCTCTTCCGATCTGTCTCGTGGGCTCGG

*FIG. 13*

Bead related primer definitions for homoadapter chemistry

*Bead option 5 (compared to bead option 2, the universal sequence is moved 3' of the bead barcode:*

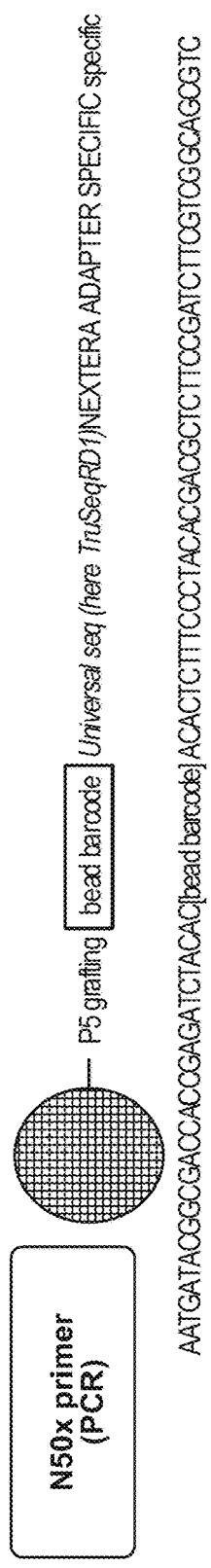

AATGATACGGCGACCACCGAGATCTACAC[bead barcode]ACACTCTTTCCCTACACGACGCTCTTCCGATCTTCGTCGGCAGCGTC

*Bead option 6 (compared to bead option 4, the universal sequence is moved 3' of the bead barcode:*

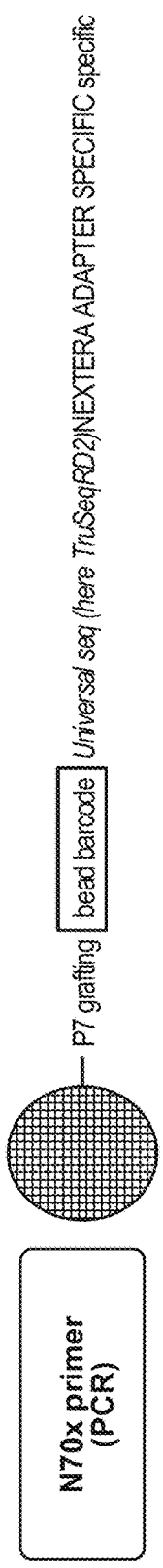

CAAGCAGAAGACGGCATACGAGAT[bead barcode]GTGACTGGAGTTCAGACGTGTGCTCTTCCGATCTGTCTCGTGGGCTCGG

*FIG. 14*

Homoadapter Tn5 biochemistry, bead option 5 and sequencing – PCR suppression of amplicons with the same ends AATGATACGGCGACCACCGAGATCTACAC[beadbarcode]ACACTCTTTCCCTACACGACGCTCTTCCGATCTTGTGGAAAGGACGAAACACCG[beadbarcode]GTGTAGATCTCGGTGGTCGCCGTATCATT-⌒-CTGTCTCTTATACACATCTGACGCTGCCGACGAGAGACGTGTGCTCTTCCGATCTCGGTGTTTCGTCCTTTCCACAAGATATCGGAAGAGCGTCGTGTAGGGAAAGAGTGT[beadbarcode]GTGTAGATCTCGGTGGTCGCCGTATCATT

PCR suppression bead adapters on both ends

CAAGCAGAAGACGGCATACGAGAT[i7]GTGACTGGAGTTCAGACGTGTGCTCTTCCGATCTTGTGGAAAGGACGAAACACCG[i7]ATCTCGTATGCCGTCTTCTGCTTG-⌒-CTGTCTCTTATACACATCTGACGCTGCCGACGAGAGACGTGTGCTCTTCCGATCGAAGAGCACACGTCTGAACTCCAGTCAC[i7]ATCTCGTATGCCGTCTTCTGCTTG

PCR suppression solution primers on both ends

NB: Even if some amplicons make it through to the final library they will not form productive clusters on the flow cell

*FIG. 17*

Homoadapter Tn5 biochemistry, bead option 6 and sequencing – PCR suppression of amplicons with the same ends bead adapters on both ends:
CAAGCAGAAGACGGCATACGAGAT[bead barcode]GTGACTGGAGTTCAGACGTGTGCTCTTCCGATCTGTGCTCTTCCGATCTGACTCCAGTCAC[bead barcode]ATCTCGTATGCCGTCTTCTGCTTG
CTTGTCGTCTTCTGCCGTATGCTCTA[bead barcode]CACTGACCTCAAGTCTGCACACGAGAAGGCTAG...ACACGAGAAGGCTAG[bead barcode]TAGAGCATACGGCAGAAGACGAAC PCR suppression solution primers on both ends:
AATGATACGGCGACCACCGAGATCTACAC[i5]ACACTCTTTCCCTACACGACGCTCTTCCGATCTGTGCTCTTCCGATCTGGAGAAGAGTGT[i5]GTGTAGATCTCGGTGGTCGCCGTATCATT
TTACTATGCCGCTGGTGGCTCTAGATGTG[i5]TGTGAGAAAGGGATGTGCTGCGAGAAGGCTAGACACGAGAAGGCTAG...CCTCTTCTCACA[i5]CACATCTAGAGCCACCAGCGGCATAGTAA PCR suppression

*NB: Even if some amplicons make it through to the final library, they will not form productive clusters on the flow cell*

*FIG. 20*

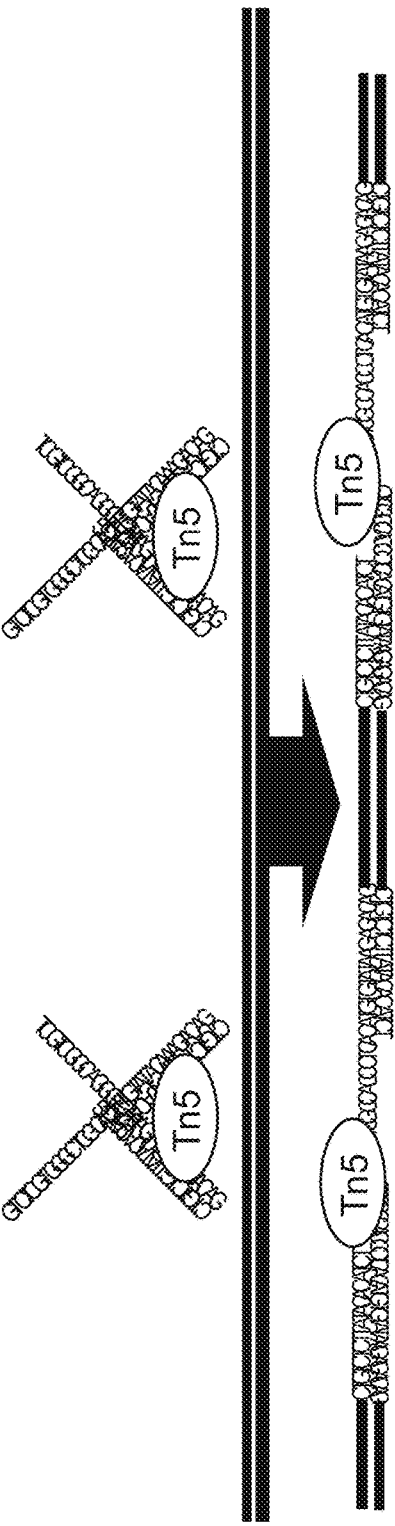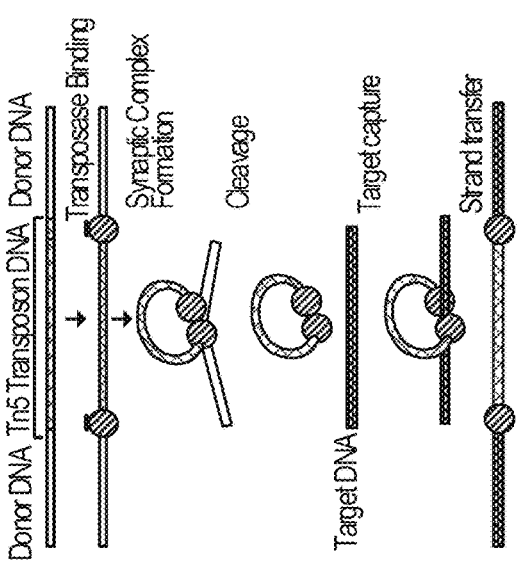
FIG. 21

Option 7:

N50x primer (PCR) — P5 grafting – INDEX – NEXTERA ADAPTER specific (A14)–common NE mosaic end
AATGATACGGCGACCACCGAGATCTACAC[i5]TCGTCGGCAGCGTCAGATGTGTATAAGAGACAG N70x primer (PCR) — P7 grafting – INDEX – NEXTERA ADAPTER specific (B15)–common NE mosaic end
CAAGCAGAAGACGGCATACGAGAT[i7]GTCTCGTGGGCTCGGAGATGTGTATAAGAGACAG Option 8:

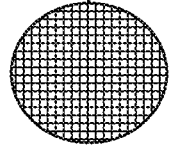 N50x primer (PCR) — P5 grafting [bead barcode] NEXTERA ADAPTER specific–common NE mosaic end
AATGATACGGCGACCACCGAGATCTACAC[beadbarcode]TCGTCGGCAGCGTCAGATGTGTATAAGAGACAG

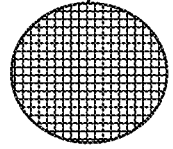 N70x primer (PCR) — P7 grafting [bead barcode] NEXTERA ADAPTER specific–common NE mosaic end
CAAGCAGAAGACGGCATACGAGAT[beadbarcode]GTCTCGTGGGCTCGGAGATGTGTATAAGAGACAG

FIG. 25

*CPT ddSEQ projected performance*

| WGS | Beads in bulk (Zhang et al 2017 Nature Biotech) | 10X Genomics (Zheng et al 2016 Nature Biotech) | CPTseq in droplets expected results |
|---|---|---|---|
| Fold coverage | 19X | 31-37X | >30X |
| % aligned | 75% | 95-97% | >80% |
| % duplication | 21% | 0.5-6% | <5% |
| Genome equivalents per drop | 0.26% | 0.11-0.44% | <0.4% |
| Barcode>10K reads | 147K | 111-150K | >100K |
| Average island length | 58kb | 38-75kb | >20kb |
| SNPs phased | 98% | 95-99% | >95% |
| N50 phase block | 1.1Mb | 0.89-2.8 Mb | >1Mb |
| Short switch SNP error | 0.13% | 0.01-0.93% | <1% |
| Long switch error | 0.0085% | 0.01-0.09% | <0.1% |

*FIG. 31*

SEQUENCE LISTING

```
<160> NUMBER OF SEQ ID NOS: 57

<210> SEQ ID NO 1
<211> LENGTH: 53
<212> TYPE: DNA
<213> ORGANISM: Artificial Sequence
<220> FEATURE:
<223> OTHER INFORMATION: synthetic oligonucleotide construct

<400> SEQUENCE: 1
tttttttuuu ctacacgcct gtccgcggaa gcagtggtat caacgcagag tac        53

<210> SEQ ID NO 2
<211> LENGTH: 16
<212> TYPE: DNA
<213> ORGANISM: Artificial Sequence
<220> FEATURE:
<223> OTHER INFORMATION: synthetic oligonucleotide construct

<400> SEQUENCE: 2
tactctgcgt tgatac                                                  16

<210> SEQ ID NO 3
<211> LENGTH: 36
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (16)..(21)
<223> OTHER INFORMATION: N is A, C, G or T

<400> SEQUENCE: 3
tagttgcgtc tcatgnnnnn natcggtagc gtaacg                            36

<210> SEQ ID NO 4
<211> LENGTH: 37
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (17)..(22)
<223> OTHER INFORMATION: N is A, C, G or T

<400> SEQUENCE: 4
tagttgcgtc tcatgcnnnn nnatcggtag cgtaacg                           37

<210> SEQ ID NO 5
<211> LENGTH: 38
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
```

```
<222> LOCATION: (18)..(23)
<223> OTHER INFORMATION: N is A, C, G or T

<400> SEQUENCE: 5
tagttgcgtc tcatgttnnn nnnatcggta gcgtaacg                            38

<210> SEQ ID NO 6
<211> LENGTH: 39
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (19)..(24)
<223> OTHER INFORMATION: N is A, C, G or T

<400> SEQUENCE: 6
tagttgcgtc tcatgagcnn nnnnatcggt agcgtaacg                           39

<210> SEQ ID NO 7
<211> LENGTH: 40
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (20)..(25)
<223> OTHER INFORMATION: N is A, C, G or T

<400> SEQUENCE: 7
tagttgcgtc tcatgatccn nnnnatcgg tagcgtaacg                           40

<210> SEQ ID NO 8
<211> LENGTH: 41
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (21)..(26)
<223> OTHER INFORMATION: N is A, C, G or T

<400> SEQUENCE: 8
tagttgcgtc tcatggcgga nnnnnnatcg gtagcgtaac g                        41

<210> SEQ ID NO 9
<211> LENGTH: 74
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (54)..(59)
<223> OTHER INFORMATION: N is A, C, G or T

<400> SEQUENCE: 9
tttttttuuu ctacacgcct gtccgcggaa gcagtggtat caacgcagag tacnnnnnnt    60
agccatcgca ttgc                                                     74

<210> SEQ ID NO 10
<211> LENGTH: 14
<212> TYPE: DNA
<213> ORGANISM: Artificial Sequence
<220> FEATURE:
```

```
<223> OTHER INFORMATION: synthetic oligonucleotide construct

<400> SEQUENCE: 10
caatgcgatg gcta                                                         14

<210> SEQ ID NO 11
<211> LENGTH: 36
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (16)..(21)
<223> OTHER INFORMATION: N is A, C, G or T

<400> SEQUENCE: 11
atcggtagcg taacgnnnnn natggtgact cgactt                                 36

<210> SEQ ID NO 12
<211> LENGTH: 95
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (54)..(59)
<223> OTHER INFORMATION: N is A, C, G or T
<220> FEATURE:
<221> NAME/KEY: misc_feature
<222> LOCATION: (75)..(80)
<223> OTHER INFORMATION: N is A, C, G or T

<400> SEQUENCE: 12 ttttttuuu ctacacgcct gtccgcggaa gcagtggtat caacgcagag tacnnnnnnt        60
agccatcgca ttgcnnnnnn taccactgag ctgaa                                  95

<210> SEQ ID NO 13
<211> LENGTH: 15
<212> TYPE: DNA
<213> ORGANISM: Artificial Sequence
<220> FEATURE:
<223> OTHER INFORMATION: synthetic oligonucleotide construct

<400> SEQUENCE: 13
ttcagctcag tggta                                                        15

<210> SEQ ID NO 14
<211> LENGTH: 52
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (11)..(16)
<223> OTHER INFORMATION: N is A, C, G or T
<220> FEATURE:
<221> NAME/KEY: misc_feature
<222> LOCATION: (32)..(37)
<223> OTHER INFORMATION: N is A, C, G or T

<400> SEQUENCE: 14
cgcagagtac nnnnnntagc catcgcattg cnnnnnntac ctctgagctg aa               52

<210> SEQ ID NO 15
<211> LENGTH: 35
```

```
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (16)..(21)
<223> OTHER INFORMATION: N is A, C, G or T

<400> SEQUENCE: 15
atggagactc gacttnnnnn nagcagccgt cgcag                                35

<210> SEQ ID NO 16
<211> LENGTH: 72
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (11)..(16)
<223> OTHER INFORMATION: N is A, C, G or T
<220> FEATURE:
<221> NAME/KEY: misc_feature
<222> LOCATION: (32)..(37)
<223> OTHER INFORMATION: N is A, C, G or T
<220> FEATURE:
<221> NAME/KEY: misc_feature
<222> LOCATION: (53)..(58)
<223> OTHER INFORMATION: N is A, C, G or T

<400> SEQUENCE: 16
cgcagagtac nnnnnntagc catcgcattg cnnnnnntac ctctgagctg aannnnnntc     60
gtcggcagcg tc                                                         72

<210> SEQ ID NO 17
<211> LENGTH: 14
<212> TYPE: DNA
<213> ORGANISM: Artificial Sequence
<220> FEATURE:
<223> OTHER INFORMATION: synthetic oligonucleotide construct

<400> SEQUENCE: 17
gacgctgccg acga                                                       14

<210> SEQ ID NO 18
<211> LENGTH: 115
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (68)..(73)
<223> OTHER INFORMATION: N is A, C, G or T
<220> FEATURE:
<221> NAME/KEY: misc_feature
<222> LOCATION: (89)..(94)
<223> OTHER INFORMATION: N is A, C, G or T
<220> FEATURE:
<221> NAME/KEY: misc_feature
<222> LOCATION: (110)..(115)
<223> OTHER INFORMATION: N is A, C, G or T

<400> SEQUENCE: 18
tttttttuuu ctacacgcct gtccgcggaa gcagtggtat caacgcagag tactcgtcgg     60
cagcgtcnnn nnntagccat cgcattcgnn nnntaccac tgagctgaan nnnn           115

<210> SEQ ID NO 19
```

```
<211> LENGTH: 33
<212> TYPE: DNA
<213> ORGANISM: Artificial Sequence
<220> FEATURE:
<223> OTHER INFORMATION: synthetic oligonucleotide construct

<400> SEQUENCE: 19
tcgtcggcag cgtcagatgt gtataagaga cag                              33

<210> SEQ ID NO 20
<211> LENGTH: 19
<212> TYPE: DNA
<213> ORGANISM: Artificial Sequence
<220> FEATURE:
<223> OTHER INFORMATION: synthetic oligonucleotide construct

<400> SEQUENCE: 20
ctgtctctta tacacatct                                              19

<210> SEQ ID NO 21
<211> LENGTH: 34
<212> TYPE: DNA
<213> ORGANISM: Artificial Sequence
<220> FEATURE:
<223> OTHER INFORMATION: synthetic oligonucleotide construct

<400> SEQUENCE: 21
gtctcgtggg ctcggagatg tgtataagag acag                             34

<210> SEQ ID NO 22
<211> LENGTH: 51
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (30)..(37)

<400> SEQUENCE: 22
aatgatacgg cgaccaccga gatctacacn nnnnnnntcg tcggcagcgt c           51

<210> SEQ ID NO 23
<211> LENGTH: 47
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (25)..(32)
<223> OTHER INFORMATION: N is A, C, G or T

<400> SEQUENCE: 23
caagcagaag acggcatacg agatnnnnnn nngtctcgtg ggctcgg                47

<210> SEQ ID NO 24
<211> LENGTH: 29
<212> TYPE: DNA
<213> ORGANISM: Artificial Sequence
<220> FEATURE:
<223> OTHER INFORMATION: synthetic oligonucleotide construct

<400> SEQUENCE: 24
aatgatacgg cgaccaccga gatctacac                                   29

<210> SEQ ID NO 25
```

<211> LENGTH: 14
<212> TYPE: DNA
<213> ORGANISM: Artificial Sequence
<220> FEATURE:
<223> OTHER INFORMATION: synthetic oligonucleotide construct

<400> SEQUENCE: 25
tcgtcggcag cgtc                                                     14

<210> SEQ ID NO 26
<211> LENGTH: 33
<212> TYPE: DNA
<213> ORGANISM: Artificial Sequence
<220> FEATURE:
<223> OTHER INFORMATION: synthetic oligonucleotide construct

<400> SEQUENCE: 26
acactctttc cctacacgac gctcttccga tct                                33

<210> SEQ ID NO 27
<211> LENGTH: 24
<212> TYPE: DNA
<213> ORGANISM: Artificial Sequence
<220> FEATURE:
<223> OTHER INFORMATION: synthetic oligonucleotide construct

<400> SEQUENCE: 27
caagcagaag acggcatacg agat                                          24

<210> SEQ ID NO 28
<211> LENGTH: 15
<212> TYPE: DNA
<213> ORGANISM: Artificial Sequence
<220> FEATURE:
<223> OTHER INFORMATION: synthetic oligonucleotide construct

<400> SEQUENCE: 28
gtctcgtggg ctcgg                                                    15

<210> SEQ ID NO 29
<211> LENGTH: 58
<212> TYPE: DNA
<213> ORGANISM: Artificial Sequence
<220> FEATURE:
<223> OTHER INFORMATION: synthetic oligonucleotide construct

<400> SEQUENCE: 29
caagcagaag acggcatacg agatgtgact ggagttcaga cgtgtgctct tccgatct     58

<210> SEQ ID NO 30
<211> LENGTH: 34
<212> TYPE: DNA
<213> ORGANISM: Artificial Sequence
<220> FEATURE:
<223> OTHER INFORMATION: synthetic oligonucleotide construct

<400> SEQUENCE: 30
ctgtctctta tacacatctc cgagcccacg agac                               34

<210> SEQ ID NO 31
<211> LENGTH: 66
<212> TYPE: DNA
<213> ORGANISM: Artificial Sequence
<220> FEATURE:
<223> OTHER INFORMATION: synthetic oligonucleotide construct

<400> SEQUENCE: 31
acactctttc cctacacgac gctcttccga tcttcgtcgg cagcgtcaga tgtgtataag    60
agacag    66

<210> SEQ ID NO 32
<211> LENGTH: 66
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (35)..(42)
<223> OTHER INFORMATION: N is A, C, G or T

<400> SEQUENCE: 32
ctgtctctta tacacatctc cgagcccacg agacnnnnnn nnatctcgta tgccgtcttc    60
tgcttg    66

<210> SEQ ID NO 33
<211> LENGTH: 62
<212> TYPE: DNA
<213> ORGANISM: Artificial Sequence
<220> FEATURE:
<223> OTHER INFORMATION: synthetic oligonucleotide construct

<400> SEQUENCE: 33
aatgatacgg cgaccaccga gatctacaca cactctttcc ctacacgacg ctcttccgat    60
ct    62

<210> SEQ ID NO 34
<211> LENGTH: 65
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (34)..(41)
<223> OTHER INFORMATION: N is A, C, G or T

<400> SEQUENCE: 34
ctgtctctta tacacatccc gagcccacga gacnnnnnnn natctcgtat gccgtcttct    60
gcttg    65

<210> SEQ ID NO 35
<211> LENGTH: 70
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (30)..(37)
<223> OTHER INFORMATION: N is A, C, G or T

<400> SEQUENCE: 35
aatgatacgg cgaccaccga gatctacacn nnnnnnntcg tcggcagcgt cagatgtgta    60
taagagacag    70

<210> SEQ ID NO 36
<211> LENGTH: 24
<212> TYPE: DNA
<213> ORGANISM: Artificial Sequence
<220> FEATURE:

<223> OTHER INFORMATION: synthetic oligonucleotide construct

<400> SEQUENCE: 36
atctcgtatg ccgtcttctg cttg                                                24

<210> SEQ ID NO 37
<211> LENGTH: 58
<212> TYPE: DNA
<213> ORGANISM: Artificial Sequence
<220> FEATURE:
<223> OTHER INFORMATION: synthetic oligonucleotide construct

<400> SEQUENCE: 37
agatcggaag agcacacgtc tgaactccag tcacatctcg tatgccgtct tctgcttg           58

<210> SEQ ID NO 38
<211> LENGTH: 80
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (25)..(32)
<223> OTHER INFORMATION: N is A, C, G or T

<400> SEQUENCE: 38
caagcagaag acggcatacg agatnnnnnn nngtgactgg agttcagacg tgtgctcttc         60
cgatcttcgt cggcagcgtc                                                    80

<210> SEQ ID NO 39
<211> LENGTH: 85
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (30)..(37)
<223> OTHER INFORMATION: N is A, C, G or T

<400> SEQUENCE: 39
aatgatacgg cgaccaccga gatctacacn nnnnnnnaca ctctttccct acacgacgct         60
cttccgatct gtctcgtggg ctcgg                                              85

<210> SEQ ID NO 40
<211> LENGTH: 47
<212> TYPE: DNA
<213> ORGANISM: Artificial Sequence
<220> FEATURE:
<223> OTHER INFORMATION: synthetic oligonucleotide construct

<400> SEQUENCE: 40
acactctttc cctacacgac gctcttccga tcttcgtcgg cagcgtc                      47

<210> SEQ ID NO 41
<211> LENGTH: 49
<212> TYPE: DNA
<213> ORGANISM: Artificial Sequence
<220> FEATURE:
<223> OTHER INFORMATION: synthetic oligonucleotide construct

<400> SEQUENCE: 41
gtgactggag ttcagacgtg tgctcttccg atctgtctcg tgggctcgg                    49

```
<210> SEQ ID NO 42
<211> LENGTH: 85
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (54)..(61)
<223> OTHER INFORMATION: N is A, C, G or T

<400> SEQUENCE: 42
ctgtctctta tacacatcta gatcggaaga gcacacgtct gaactccagt cacnnnnnnn    60
natctcgtat gccgtcttct gcttg                                          85

<210> SEQ ID NO 43
<211> LENGTH: 99
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (68)..(75)
<223> OTHER INFORMATION: N is A, C, G or T

<400> SEQUENCE: 43
ctgtctctta tacacatctg acgctgccga cgaagatcgg aagagcacac gtctgaactc    60
cagtcacnnn nnnnnatctc gtatgccgtc ttctgcttg                           99

<210> SEQ ID NO 44
<211> LENGTH: 66
<212> TYPE: DNA
<213> ORGANISM: Artificial Sequence
<220> FEATURE:
<223> OTHER INFORMATION: synthetic oligonucleotide construct

<400> SEQUENCE: 44
ctgtctctta tacacatctg acgctgccga cgaagatcgg aagagcgtcg tgtagggaaa    60
gagtgt                                                               66

<210> SEQ ID NO 45
<211> LENGTH: 29
<212> TYPE: DNA
<213> ORGANISM: Artificial Sequence
<220> FEATURE:
<223> OTHER INFORMATION: synthetic oligonucleotide construct

<400> SEQUENCE: 45
gtgtagatct cggtggtcgc cgtatcatt                                      29

<210> SEQ ID NO 46
<211> LENGTH: 99
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (68)..(75)
<223> OTHER INFORMATION: N is A, C, G or T

<400> SEQUENCE: 46
ctgtctctta tacacatctg acgctgccga cgaagatcgg aagagcacac gtctgaactc    60
cagtcacnnn nnnnnatctc gtatgccgtc ttctgcttg                           99
```

```
<210> SEQ ID NO 47
<211> LENGTH: 104
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (30)..(37)
<223> OTHER INFORMATION: N is A, C, G or T

<400> SEQUENCE: 47
aatgatacgg cgaccaccga gatctacacn nnnnnnnaca ctctttccct acacgacgct      60
cttccgatct gtctcgtggg ctcggagatg tgtataagag acag                     104

<210> SEQ ID NO 48
<211> LENGTH: 68
<212> TYPE: DNA
<213> ORGANISM: Artificial Sequence
<220> FEATURE:
<223> OTHER INFORMATION: synthetic oligonucleotide construct

<400> SEQUENCE: 48
ctgtctctta tacacatctc cgagcccacg agacagatcg aagagcaca cgtctgaact       60 ccagtcac                                                              68

<210> SEQ ID NO 49
<211> LENGTH: 24
<212> TYPE: DNA
<213> ORGANISM: Artificial Sequence
<220> FEATURE:
<223> OTHER INFORMATION: synthetic oligonucleotide construct

<400> SEQUENCE: 49
atctcgtatg ccgtcttctg cttg                                            24

<210> SEQ ID NO 50
<211> LENGTH: 68
<212> TYPE: DNA
<213> ORGANISM: Artificial Sequence
<220> FEATURE:
<223> OTHER INFORMATION: synthetic oligonucleotide construct

<400> SEQUENCE: 50
gtgactggag ttcagacgtg tgctcttccg atctgtctcg tgggctcgga gatgtgtata      60
agagacag                                                              68

<210> SEQ ID NO 51
<211> LENGTH: 104
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (68)..(75)
<223> OTHER INFORMATION: N is A, C, G or T

<400> SEQUENCE: 51
ctgtctctta tacacatctc cgagcccacg agacagatcg aagagcgtc gtgtagggaa       60 agagtgtnnn nnnnngtgta gatctcggtg gtcgccgtat catt                     104

<210> SEQ ID NO 52
<211> LENGTH: 19
```

```
<212> TYPE: DNA
<213> ORGANISM: Artificial Sequence
<220> FEATURE:
<223> OTHER INFORMATION: synthetic oligonucleotide construct

<400> SEQUENCE: 52
agatgtgtat aagagacag                                              19

<210> SEQ ID NO 53
<211> LENGTH: 66
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (25)..(32)
<223> OTHER INFORMATION: N is A, C, G or T

<400> SEQUENCE: 53
caagcagaag acggcatacg agatnnnnnn nngtctcgtg ggctcggaga tgtgtataag    60
agacag                                                              66

<210> SEQ ID NO 54
<211> LENGTH: 14
<212> TYPE: DNA
<213> ORGANISM: Artificial Sequence
<220> FEATURE:
<223> OTHER INFORMATION: synthetic oligonucleotide construct

<400> SEQUENCE: 54
aatgatacgg cgac                                                    14

<210> SEQ ID NO 55
<211> LENGTH: 14
<212> TYPE: DNA
<213> ORGANISM: Artificial Sequence
<220> FEATURE:
<223> OTHER INFORMATION: synthetic oligonucleotide construct

<400> SEQUENCE: 55
caagcagaag acgg                                                    14

<210> SEQ ID NO 56
<211> LENGTH: 47
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (25)..(32)
<223> OTHER INFORMATION: N is A, C, G or T

<400> SEQUENCE: 56
caagcagaag acggcatacg agatnnnnnn nngtctcgtg ggctcgg                47

<210> SEQ ID NO 57
<211> LENGTH: 99
<212> TYPE: DNA
<213> ORGANISM: Artificial Sequence
<220> FEATURE:
<223> OTHER INFORMATION: synthetic oligonucleotide construct
<220> FEATURE:
<221> NAME/KEY: misc_feature
<222> LOCATION: (25)..(32)
<223> OTHER INFORMATION: N is A, C, G or T
```

-continued

```
<400> SEQUENCE: 57
caagcagaag acggcatacg agatnnnnnn nngtgactgg agttcagacg tgtgctcttc    60
cgatcttcgt cggcagcgtc agatgtgtat aagagacag                          99
```

DROPLET TAGGING CONTIGUITY PRESERVED TAGMENTED DNA

CROSS-REFERENCE TO RELATED PATENT APPLICATIONS

The present application is a divisional of U.S. patent application Ser. No. 15/847,408, filed Dec. 19, 2017, now U.S. Pat. No. 11,021,738, issued Jun. 1, 2021, which claims benefit of priority to U.S. Provisional Patent Application No. 62/436,288, filed Dec. 19, 2016, which is incorporated by reference.

REFERENCE TO A "SEQUENCE LISTING" SUBMITTED AS ASCII TEXT FILES VIA EFS-WEB

The Sequence Listing written in file SEQ_094868-1239699-ST25.TXT created on Apr. 20, 2021, 16,374 bytes, machine format IBM-PC, MS-Windows operating system, in accordance with 37 C.F.R. §§ 1.821-to 1.825, is hereby incorporated by reference in its entirety for all purposes.

BACKGROUND OF THE INVENTION

Haplotype information can be valuable in many genetic analyses. However, it can be difficult to obtain information regarding haplotypes from many sequencing methods because contiguity is not maintained. Amini et al. *Nature Genetics* 46(12):1343-1349 describes one method of maintaining contiguity, but the method involves many separate reactions, each of which require significant enzyme (e.g., tagmentase).

BRIEF SUMMARY OF THE INVENTION

In some embodiments, a method of determining haplotype genomic sequence is provided. In some embodiments, the method comprises
providing fragments of genomic DNA;
reacting the fragments with an adapter-loaded tagmentase that creates DNA fragments defined by breakpoints in the fragments and inserts an adaptor at the break points, wherein the reacting is under conditions such that the tagmentase binds the breakpoints to form linked DNA segments in the form of DNA segment-first adaptor-tagmentase-second adaptor-(DNA segment-first adaptor-tagmentase-second adaptor)n-DNA segment, where n is any integer and "-" indicates a covalent linkage;
encapsulating the linked DNA segments into partitions, said partitions comprising:
a bead, the bead having a forward primer oligonucleotide linked to the bead by a 5' end of the forward primer oligonucleotide, the forward primer oligonucleotide having a bead-specific barcode and a 3' end specific for and complementary to the first or second adaptor;
a reverse primer oligonucleotide having a 3' end complementary to the first or second adaptor, wherein the forward primer 3' end and the reverse primer 3' end are complementary to different adaptors selected from the first adaptor and the second adaptor;
displacing the tagmentase from the segments in the partitions; performing amplification wherein the forward primer and reverse primer oligonucleotide generate amplicons from the DNA segments, such that amplicons within a partition are barcoded with the bead barcode;
combining the partitions to form a reaction mixture containing the amplicons; and nucleotide sequencing the amplicons.

In some embodiments, the partitions comprise an amount of agent that displaces the tagmentase from the segments but does not inhibit polymerization. In some embodiments, the agent is a polymerase. In some embodiments, the agent is a detergent. In some embodiments, heat displaces the tagmentase.

In some embodiments combined with any embodiment listed above, prior to amplification, the single stranded regions of inserted adaptors are filled in by DNA polymerase. In some embodiments, the fill in process displaces the tagmentase from the segments. In some embodiments combined with any embodiment listed above, prior to amplification, single stranded regions of fragmented target nucleic acids are filled in by DNA polymerase combined with any embodiment listed above. In some embodiments, the forward primer oligonucleotide is released from the bead and amplification occurs in solution.

In some embodiments combined with any embodiment listed above, the agent is a detergent. In some embodiments combined with any embodiment listed above, the detergent is sodium dodecyl sulfate (SDS). In some embodiments combined with any embodiment listed above, the concentration of SDS is 0.005-0.05% (e.g., 0.01-0.04%, e.g., 0.01-0.02%).

In some embodiments combined with any embodiment listed above, the fragments are on average between 5-10 Mb.

In some embodiments combined with any embodiment listed above, the partitions are droplets in an emulsion.

In some embodiments combined with any embodiment listed above, the encapsulating encapsulates on average 0.02-3 (e.g., 0.05-1, 0.08-0.5, e.g., 0.1, 1, 2, or 3) beads into partitions.

In some embodiments combined with any embodiment listed above, the genomic DNA is from a single cell. In some embodiments combined with any embodiment listed above, the genomic DNA is from a mammal or plant.

In some embodiments combined with any embodiment listed above, the first adaptor and the second adaptor have different sequences. In some embodiments combined with any embodiment listed above, the first adaptor and the second adaptor have 5' overhang sequences and the 5' overhang sequences are less than 50% identical.

In some embodiments combined with any embodiment listed above, the first adaptor and the second adaptor have identical sequences.

In some embodiments combined with any embodiment listed above, the first adaptor and the second adaptor are linked by a linking sequence when loaded on the tagmentase such the DNA segments are linked by both the tagmentase and the linking sequence. In some embodiments combined with any embodiment listed above, the linking sequence comprises a restriction recognition sequence and the linking sequence is cleaved by a restriction enzyme after the encapsulating and before the performing. In some embodiments combined with any embodiment listed above, the linking sequence comprises one or more uracils and the linking sequence is cleaved by a uracil-DNA N-glycosylase after the encapsulating and before the performing. In some embodiments combined with any embodiment listed above, the linking sequence comprises one or more ribonucleotide and the linking sequence is cleaved at the ribonucleotide after the encapsulating and before the performing.

In some embodiments, combined with any embodiment listed above n is an integer selected from 0-10,000.

In some embodiments combined with any embodiment listed above, the length of the DNA segment-first adaptor-tagmentase-second adaptor-(DNA segment-first adaptor-tagmentase-second adaptor)n-DNA segment is between 5 kb-10 Mb, e.g., 1 Mb-10 Mb.

In some embodiments combined with any embodiment listed above, at least 10,000 different linked DNA segments are encapsulated into different partitions.

In some embodiments combined with any embodiment listed above, the tagmentase is linked to a solid support. For example, in some embodiments the solid support is a bead that is different from the bead linked to the forward primer.

Also provided is a plurality of partitions. In some embodiments, the partitions comprise:
a bead, the bead having a forward primer oligonucleotide linked to the bead by a 5' end of the forward primer oligonucleotide, the forward primer oligonucleotide having a bead-specific barcode and a 3' end specific for and complementary to a first or second adaptor; and
a reverse primer oligonucleotide having a 3' end complementary to the first or second adaptor, wherein the forward primer 3' end and the reverse primer 3' end are complementary to different adaptors selected from the first adaptor and the second adaptor.

In some embodiments, the partitions comprise an amount of agent that displaces tagmentase from DNA but does not inhibit polymerization.

In some embodiments, the partitions further comprise: tagmentase; and genomic DNA, wherein segments of the DNA have ends defined by adaptors inserted at breakpoints created by the tagmentase in the form first adaptor-DNA segment-second adaptor.

In some embodiments, the agent is a detergent. In some embodiments, the detergent is sodium dodecyl sulfate (SDS). In some embodiments, the concentration of SDS is 0.005-0.05% (e.g., 0.01-0.04%, e.g., 0.01-0.02%).

In some embodiments, the partitions are droplets in an emulsion.

In some embodiments, the partitions comprise on average 0.02-3 (e.g., 0.05-1, 0.08-0.5, e.g., 0.1, 1, 2, or 3) beads.

In some embodiments, the genomic DNA is from a single cell. In some embodiments, the genomic DNA is from a mammal or plant.

In some embodiments, the first adaptor and the second adaptor have different sequences. In some embodiments, the first adaptor and the second adaptor are less than 50% identical.

In some embodiments, the first adaptor and the second adaptor have identical sequences.

In some embodiments, the first adaptor and the second adaptor are linked by a linking sequence in a form comprising first adaptor-DNA segment-second adaptor-(linker sequence)-first adaptor-DNA segment-second adaptor)$_n$, where n is any integer 1 or greater.

In some embodiments, the linking sequence comprises a restriction recognition sequence and optionally the partition further comprises a restriction enzyme the restriction recognition sequence.

In some embodiments, the linking sequence comprises one or more uracils and optionally the partition further comprises a uracil-DNA N-glycosylase.

In some embodiments, the linking sequence comprises one or more ribonucleotide.

In some embodiments, n is an integer selected from 1-10,000.

In some embodiments, the length of the first adaptor-DNA segment-second adaptor-(linker sequence-first adaptor-DNA segment-second adaptor)$_n$ is between 5 kb-10 Mb, e.g., 1 Mb-10 Mb.

In some embodiments, the plurality comprises at least 10,000 different partitions.

In some embodiments, the tagmentase is linked to a solid support. For example, in some embodiments the solid support is a bead that is different from the bead linked to the forward primer.

Also provided is a plurality of partitions comprising DNA segments having contiguity maintained by tagmentase. In some embodiments, the partitions comprise linked DNA segments in the form of DNA segment-first adaptor-tagmentase-second adaptor-(DNA segment-first adaptor-tagmentase-second adaptor)n-DNA segment, where n is any integer and "-" indicates a covalent linkage and wherein the linked DNA maintains contiguity compared to genomic DNA.

In some embodiments, the partitions are droplets in an emulsion.

In some embodiments, the partitions comprise on average 0.02-3 (e.g., 0.05-1, 0.08-0.5, e.g., 0.1, 1, 2, or 3) beads.

In some embodiments, the genomic DNA is from a single cell. In some embodiments, the genomic DNA is from a mammal or plant.

In some embodiments, the first adaptor and the second adaptor have different sequences. In some embodiments, the first adaptor and the second adaptor are less than 50% identical.

In some embodiments, the first adaptor and the second adaptor have identical sequences.

In some embodiments, the linking sequence comprises a restriction recognition sequence and optionally the partition further comprises a restriction enzyme the restriction recognition sequence.

In some embodiments, the linking sequence comprises one or more uracils and optionally the partition further comprises a uracil-DNA N-glycosylase.

In some embodiments, the linking sequence comprises one or more ribonucleotide.

In some embodiments, n is an integer selected from 1-10,000.

In some embodiments, the length of the first adaptor-DNA segment-second adaptor-(linker sequence-first adaptor-DNA segment-second adaptor)n is between 5 kb-10 Mb, e.g., 1 Mb-10 Mb.

In some embodiments, the plurality comprise at least 10,000 different partitions.

BRIEF DESCRIPTION OF THE DRAWINGS

FIG. 2 displays several of many configurations of primers for sequencing.

3-8, respectively); 3. Bead Oligo (SEQ ID NO:9), BC Block 1 template (SEQ ID NO:3) and probe (SEQ ID NO:10); 4. Bead Oligo (SEQ ID NO:9), BC Block 2 template (SEQ ID NO:11); 5. Bead Oligo (SEQ ID NO:12), BC Block 2 template (SEQ ID NO:11), and probe (SEQ ID NO:13)).

Figure 1:
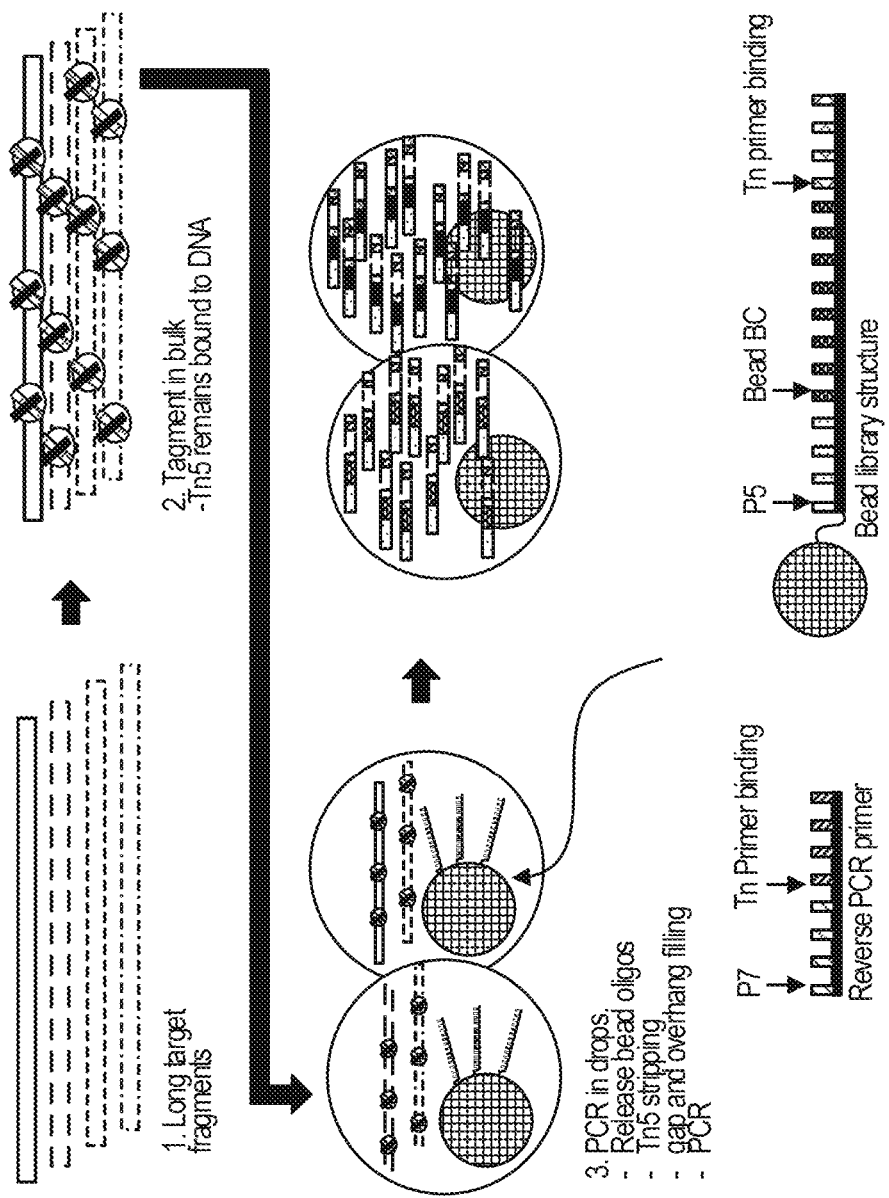
FIG. 1 illustrates the first part of a possible workflow. DNA fragments are reacted with adaptor-loaded tagmentase, encapsulated in a partition with a bead linked to a barcoded primer and second primer and amplified in the partition.
Figure 2:
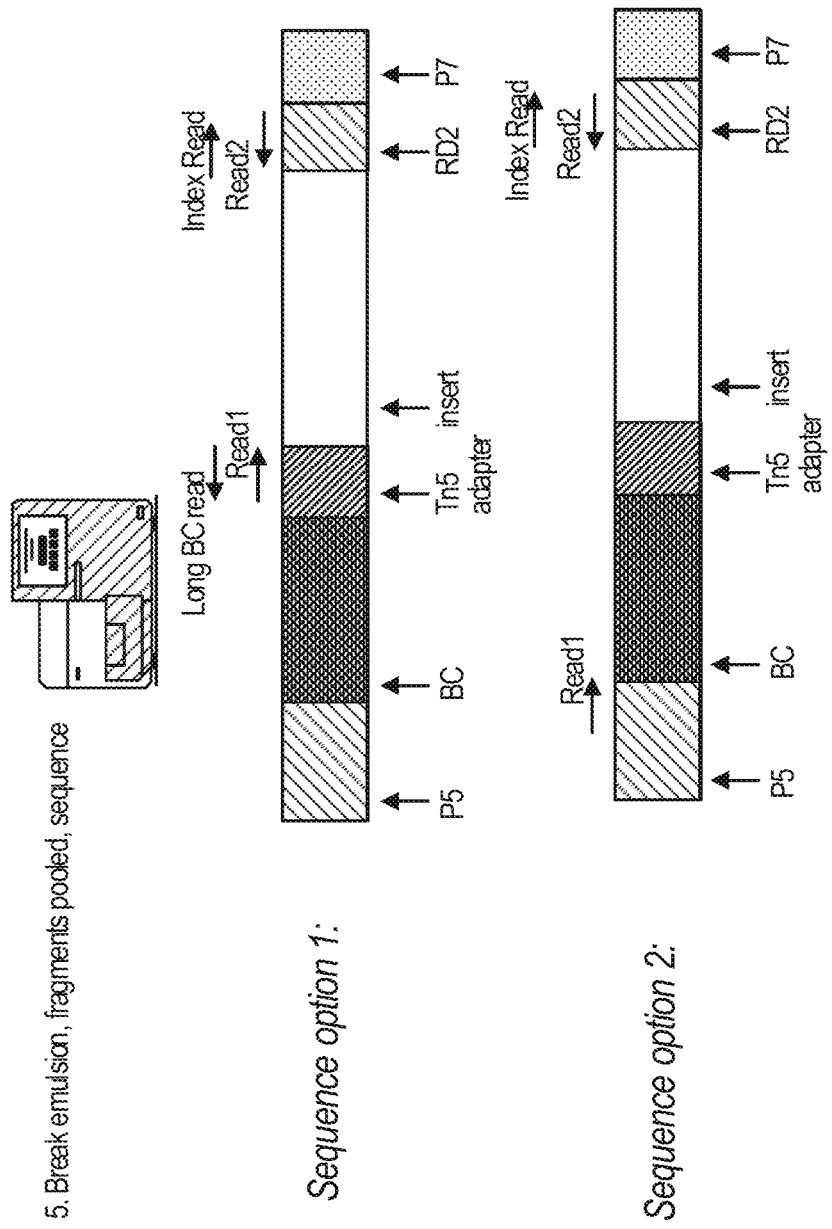
FIG. 2 illustrates the second part of a possible workflow (continued from FIG. 1). Amplicons from the partitions are mixed (for example, if droplets in an emulsion are used, the emulsion is broken and the aqueous droplets pooled). The amplicons are then sequenced.
Figure 3:
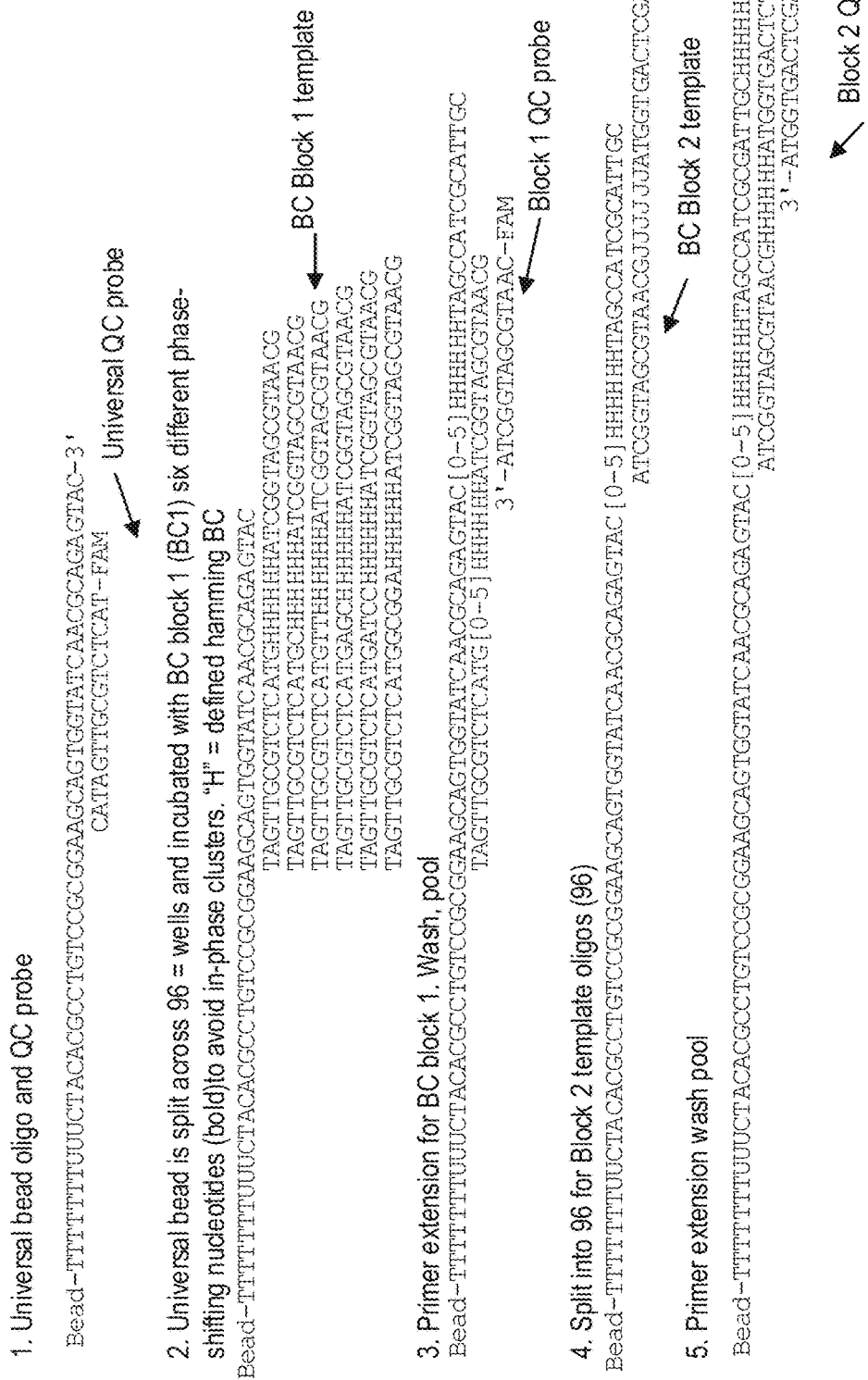
FIG. 3 depicts illustrates one possible for generating bead-linked and barcoded oligonucleotides as can be used in the methods described herein. (Sequences: 1. Bead Oligo (SEQ ID NO:1) and probe (SEQ ID NO:2); 2. Bead Oligo (SEQ ID NO:1) and BC Block 1 templates (SEQ ID NOS.

FIG. 4 is a continuation of FIG. 3. (Sequences: 6. Bead Oligo (SEQ ID NO:14) and block 3 template (SEQ ID NO:15); 7. Bead Oligo (SEQ ID NO:16), adapter sequence (SEQ ID NO:15); probe (SEQ ID NO: 17); 8. BC Bead oligo (SEQ ID NO: 18)).

Figure 5:
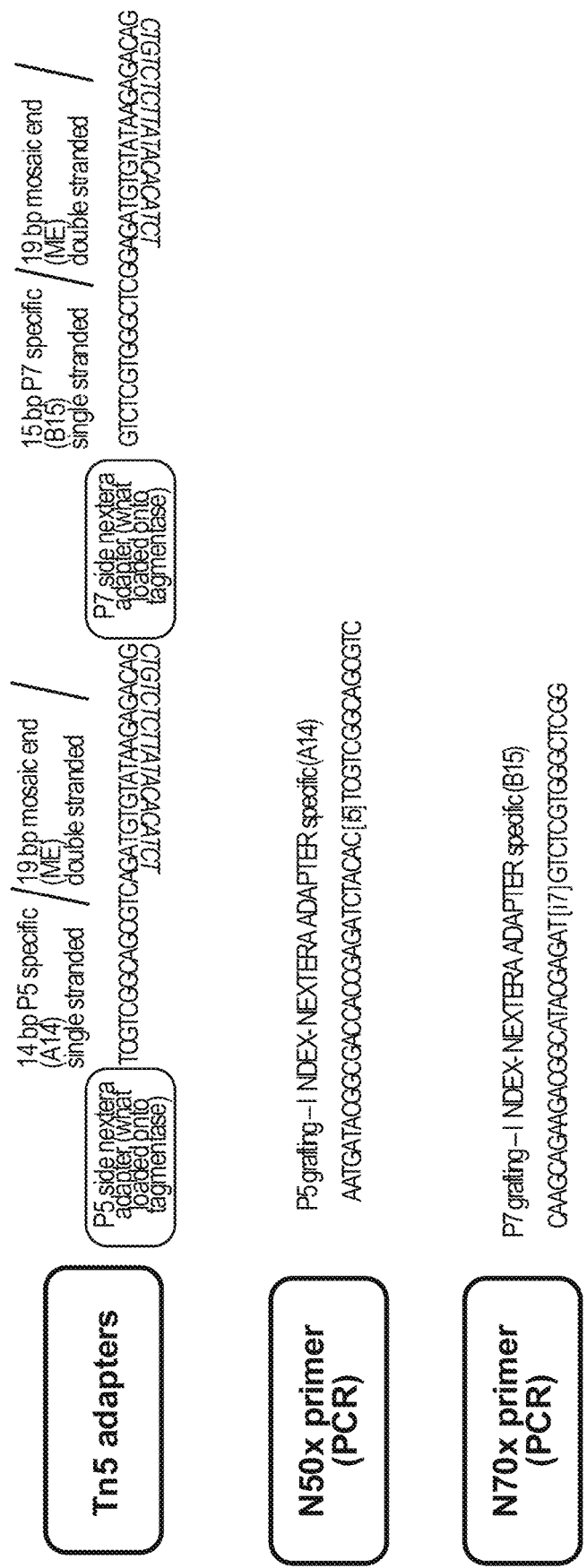

FIG. 5 depicts exemplary tagmentase (Tn5) adaptors and amplification primers that can be used to amplify DNA segments having the adaptors. (Sequences—adapters P5 (SEQ ID NOS:19-20) and P7 (SEQ ID NOS:21 and 20); primers P5/N50x/[i5] (SEQ ID NO:22) and P7/N70x/[i7] (SEQ ID NO:23)).

FIG. 6 illustrates various possible non-limiting options for the bead-linked oligonucleotide primer. (Sequences: previous N50x (SEQ ID NO:22); Option 1 P5 grafting (SEQ ID NO:24) and adapter-specific (SEQ ID NO:25); and Option 2 P5 grafting (SEQ ID NO:26) and adapter-specific (SEQ ID NO:25)).

FIG. 7 illustrates additional possible non-limiting options for the bead-linked oligonucleotide primer. (Sequences: previous N70x (SEQ ID NO:23); Option 1 P7 grafting (SEQ ID NO:27) and adapter-specific (SEQ ID NO:28); and Option 2 P5 grafting (SEQ ID NO:29) and adapter-specific (SEQ ID NO:28)).

Figure 8:
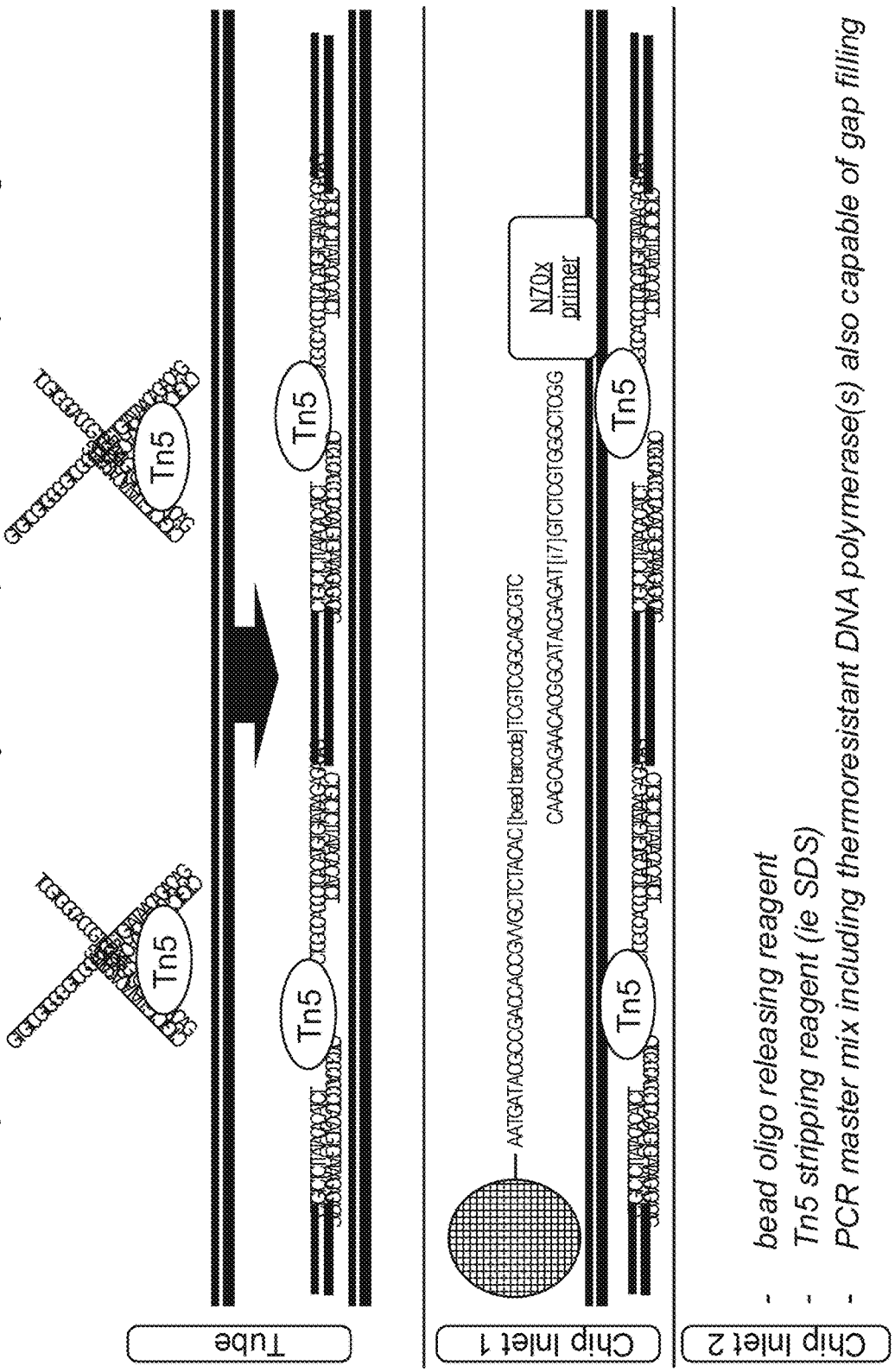

FIG. 8 depicts a possible option for using heteroadaptor-loaded tagmentase. (Sequences: Tn5 adapters (SEQ ID NOS:19-21; primer P5 grafting (SEQ ID NO:24) and adapter-specific (SEQ ID NO:25); and primer N70x (SEQ ID NO:23)).

FIG. 9 is a continuation of FIG. 8. (Sequences: Tn5 stripping (SEq ID NOS:19-21); overhang filling (SEQ ID NOS:30 and 19); PCR product (terminal side) with grafting (SEQ ID NO:24) and adapter (SEQ ID NO: 19); PCR product (carboxyl-side) with P7/[i7] primer SEQ ID NO:32).

Figure 10:
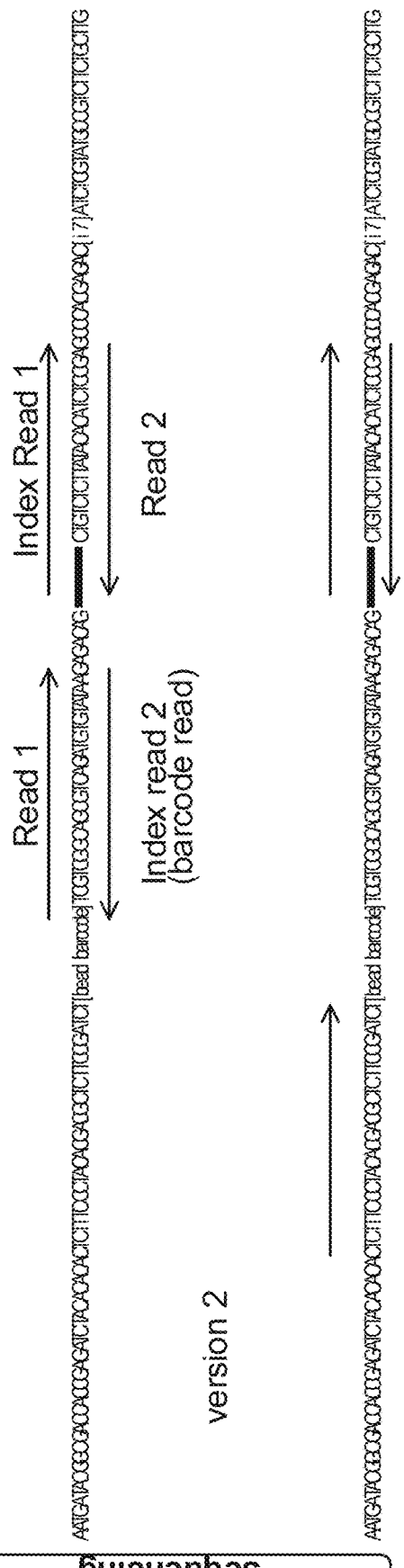

FIG. 10 depicts a possible option (different from FIG. 8) for using heteroadaptor-loaded tagmentase. (Sequences: grafting (SEQ ID NO:33) and adaptor-specific (SEQ ID NO:19); and P7/[i7] primer SEQ ID NO:34).

Figure 11:
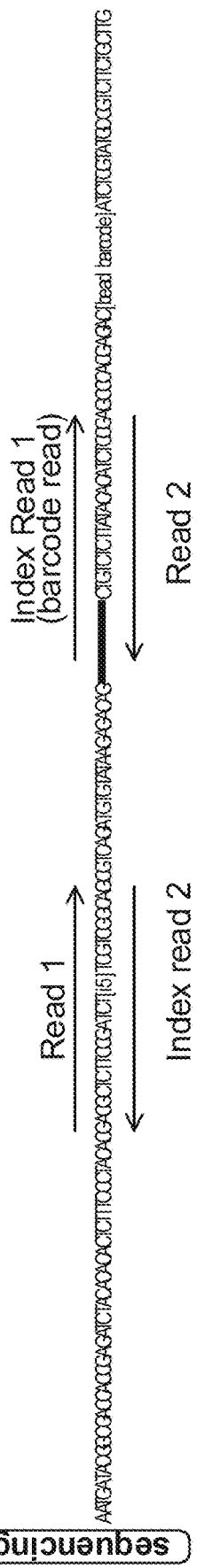

FIG. 11 depicts a possible option (different from FIG. 8 or 10) for using heteroadaptor-loaded tagmentase. (Sequences: N50x primer (SEQ ID NO:35) and carboxyl-side with grafting (SEQ ID NO:30) and adapter (SEQ ID NO;36).

Figure 12:
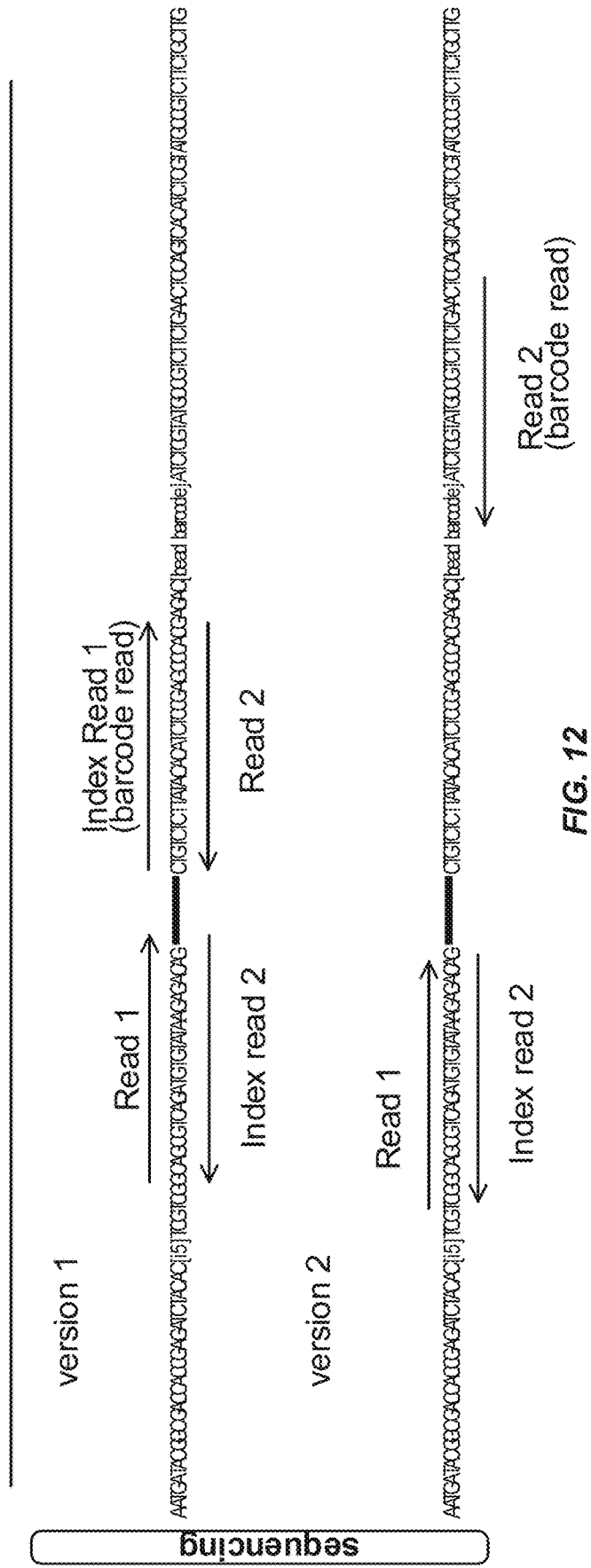

FIG. 12 depicts a possible option (different from FIG. 8, 10, or 11) for using heteroadaptor-loaded tagmentase. (Sequences: N50x primer (SEQ ID NO:35) and carboxyl-side with grafting (SEQ ID NO:30) and adapter (SEQ ID NO;37).

FIG. 13 depicts a possible option for using homoadaptor-loaded tagmentase. (Sequences: canonical N70x primer (SEQ ID NO:23) and N50x primer (SEQ ID NO:22); modified N70x primer (SEQ ID NO:38) and N50x primer (SEQ ID NO:39).

FIG. 14 depicts some possible options for primer sequences when using homoadaptor-loaded tagmentase. (Sequences: P5 grafting (SEQ ID NO:24) and adapter (SEQ ID NO:40); P7 grafting (SEQ ID NO:27) and adapter (SEQ ID NO:41)).

Figure 15:
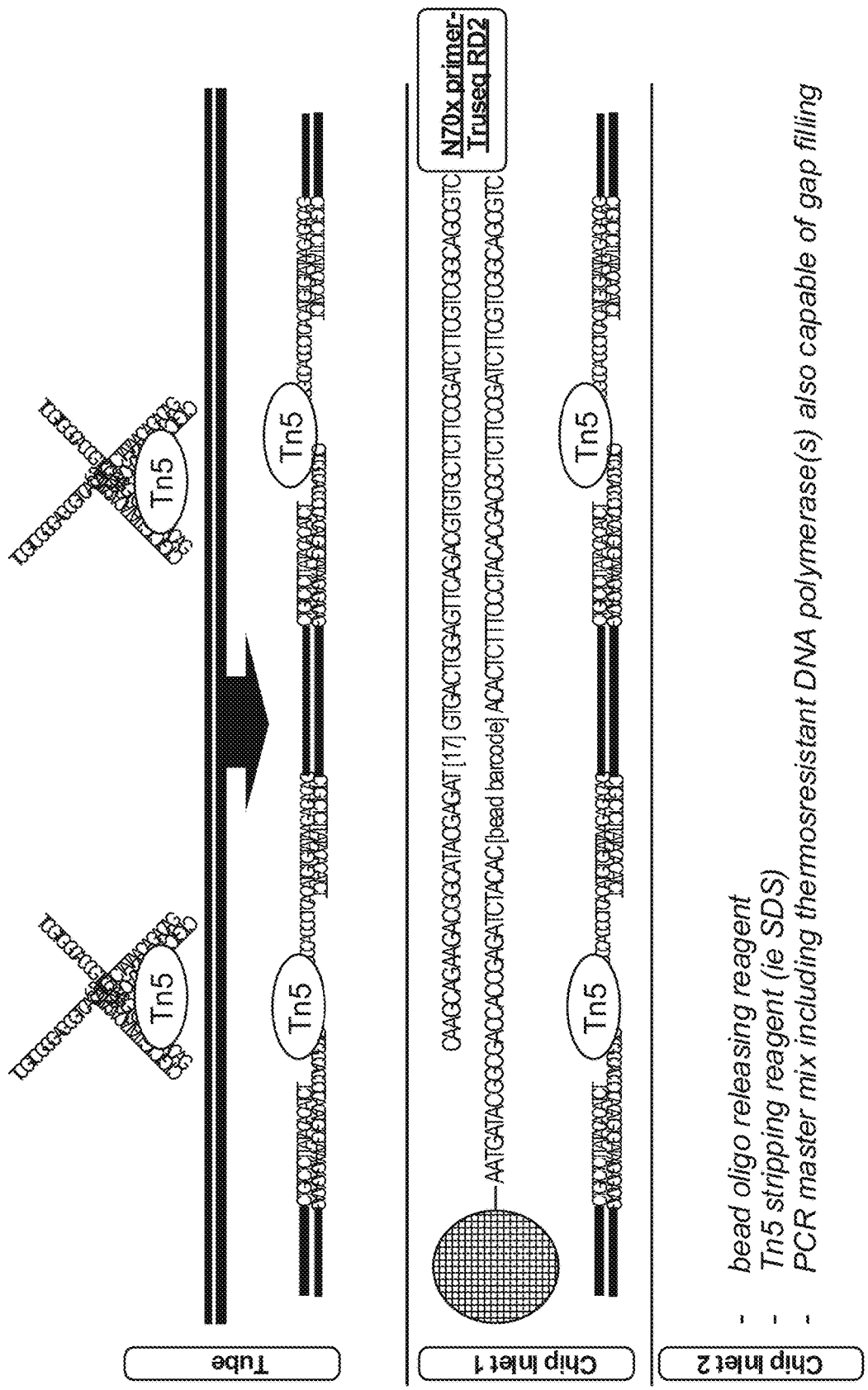

FIG. 15 depicts a possible option for using homoadaptor-loaded tagmentase. (Sequences: Tube (SEQ ID NOS:19 and 20); Inlet 1 N70x primer (SEQ ID NO:38) and bead with grafting (SEQ ID NO:24) and adapter (SEQ ID NO:40)).

Figure 16:
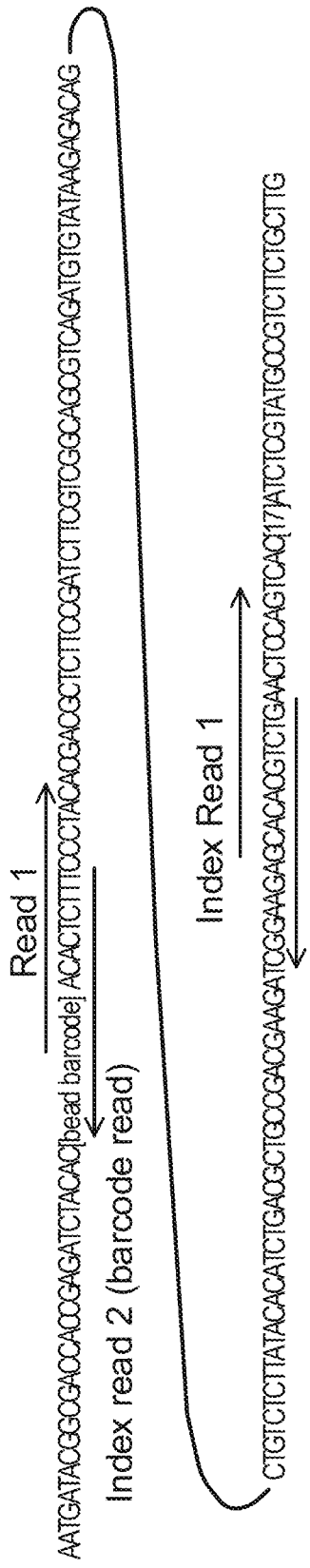

FIG. 16 is a continuation of FIG. 15. (Sequences: Terminal side of Drops (grafting (SEQ ID NO:24) and adapter (SEQ ID NO:31) and carboxyl-side of Drops (with P7/[i7] primer SEQ ID NO:42)).

FIG. 17 is a continuation of FIG. 15 and illustrates how one can use PCR suppression to preferentially inhibit homo-tailed amplicons produced by polymerase extensions within the context of using a homoadaptered Tn5 transposase. (Sequences: bead adapters on both ends (SEQ ID NOS:24, 31, 44, and 45, respectively); and primers on both ends (SEQ ID NOS:57 and 46)).

Figure 18:
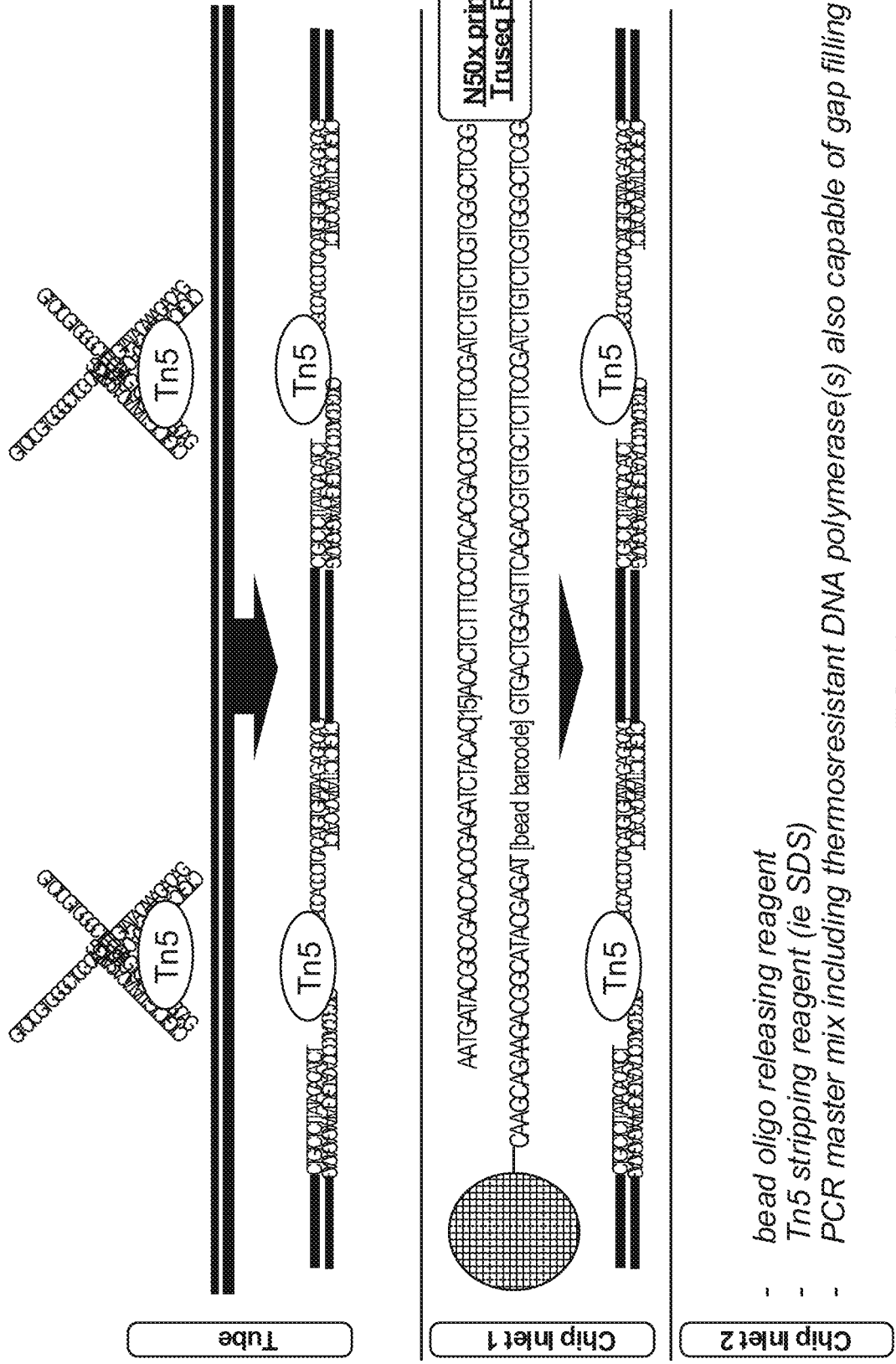

FIG. 18 depicts a possible option (different from FIG. 15) for using homoadaptor-loaded tagmentase. (Sequences: Tube adapters (SEQ ID NOS:19-21); Inlet 1 N50x primer (SEQ ID NO:39) and bead with grafting (SEQ ID NO:27) and adapter (SEQ ID NO:41)).

Figure 19:
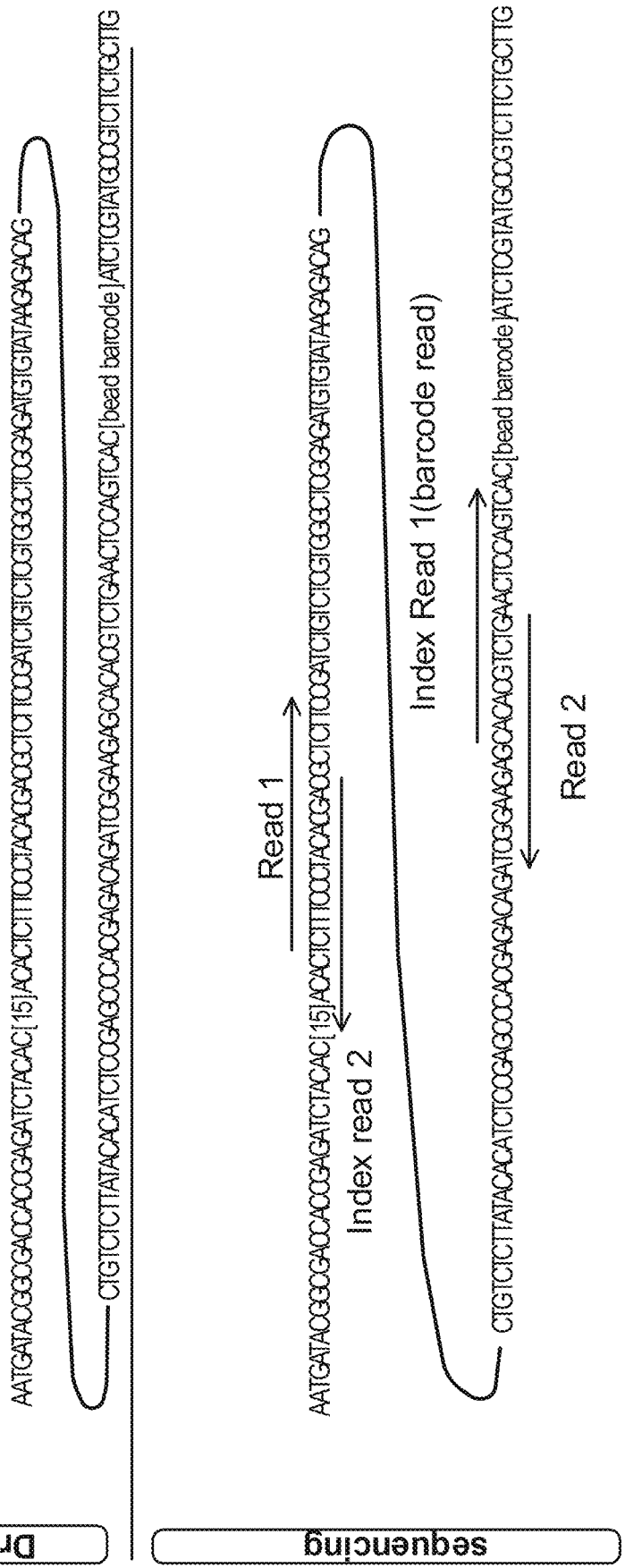

FIG. 19 is a continuation of FIG. 18. (Sequences: Terminal side of Drops (primer (SEQ ID NO:47) and carboxyl-side of drops with grafting (SEQ ID NO:48) and adapter (SEQ ID NO:49)).

FIG. 20 is a continuation of FIG. 18 and illustrates how one can use PCR suppression to preferentially inhibit homo-tailed amplicons produced by polymerase extensions within the context of using a homoadaptered Tn5 transposase. (Sequences: bead adapters on both ends (SEQ ID NOS:27, 50, 48, and 49, respectively); and primers on both ends (SEQ ID NOS:47 and 51)).

FIG. 21 depicts possible embodiments of the method as well as illustrating the mechanism of Tn5 action. (Tn5 adapter sequences SEQ ID NOS:19-21).

Figure 22:
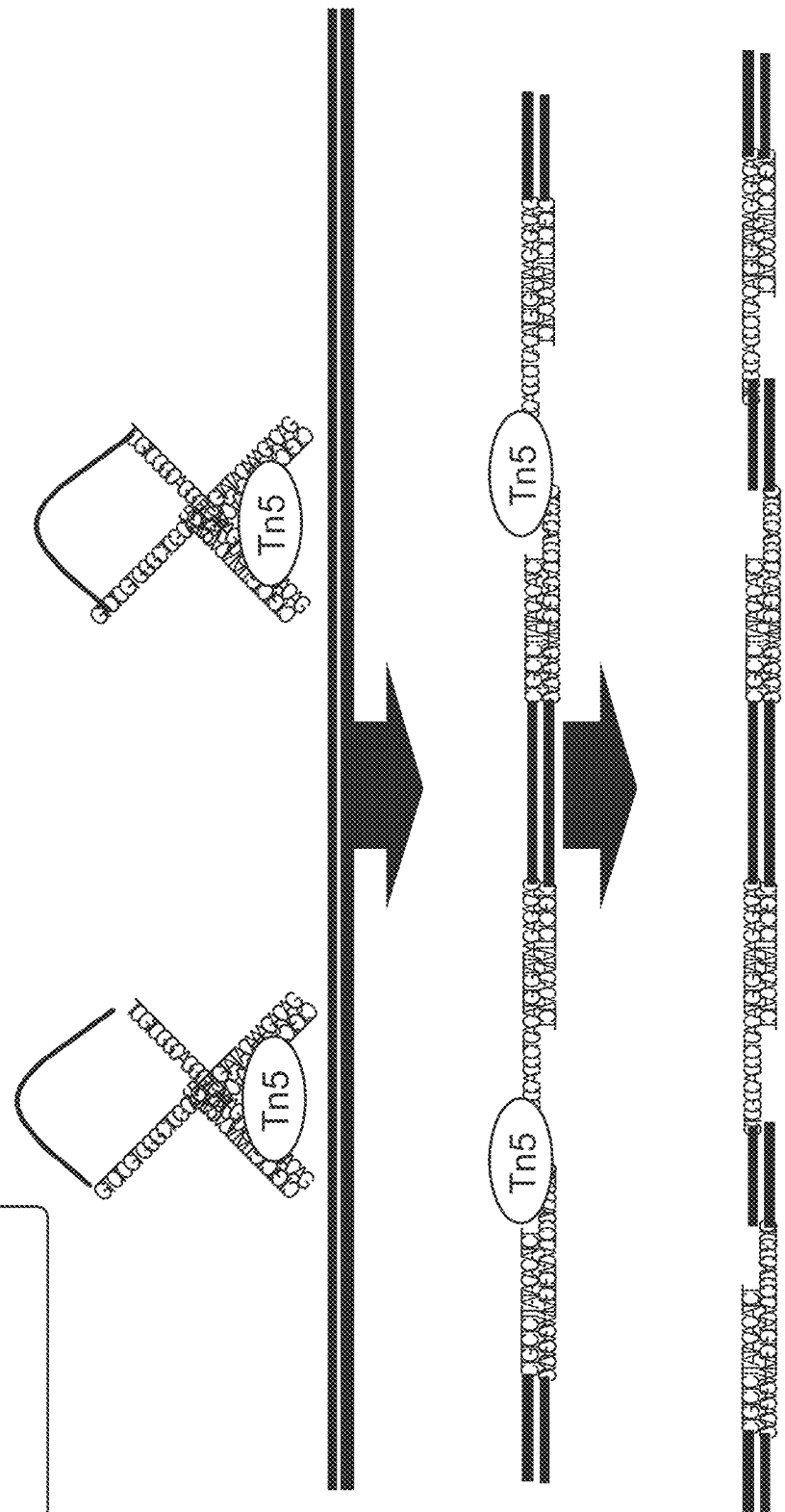

FIG. 22 depicts an option in which the two adaptors loaded on the tagmentase are linked by a linking sequence. The linking sequence is included with the adaptors inserted by the tagmentase and thus the linking sequences function to maintain contiguity of DNA segments. (Tn5 adapter sequences SEQ ID NOS:19-21).

Figure 23:
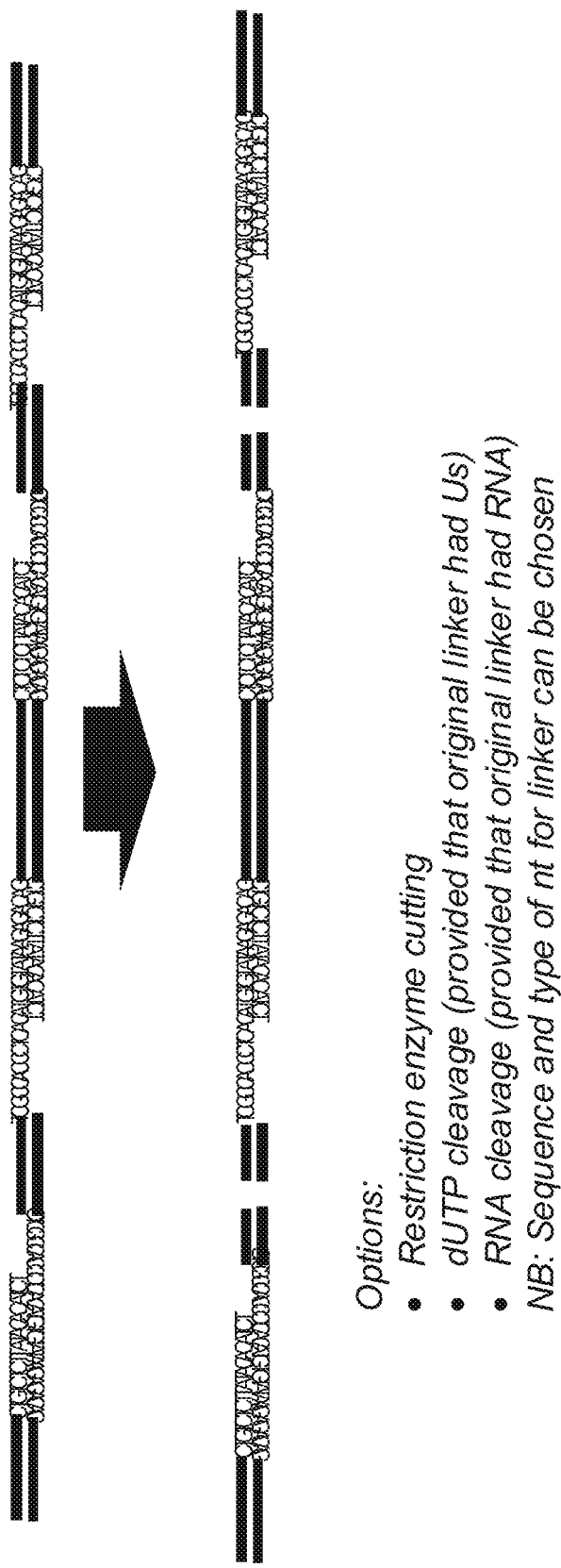

FIG. 23 is a continuation of FIG. 22 and depicts various possible options for cleaving the linking sequences, thereby releasing separate DNA segments into the partition. (Tn5 adapter sequences SEQ ID NOS:19-21).

Figure 24:

FIG. 24 depicts an exemplary adaptor for use as a homoadaptor. (SEQ ID NOS:52 and 20).

FIG. 25 illustrates possible oligonucleotide primers for use with the homoadaptor depicted in FIG. 24. (N50x primer (SEQ ID NO:35), N70x primer (SEQ ID NO:53), Option 7 N50x primer (grafting SEQ ID NO:24 and adapter SEQ ID NO:19), and Option 8 N70x primer (grafting SEQ ID NO:27 and adapter SEQ ID NO:21)).

Figure 26:
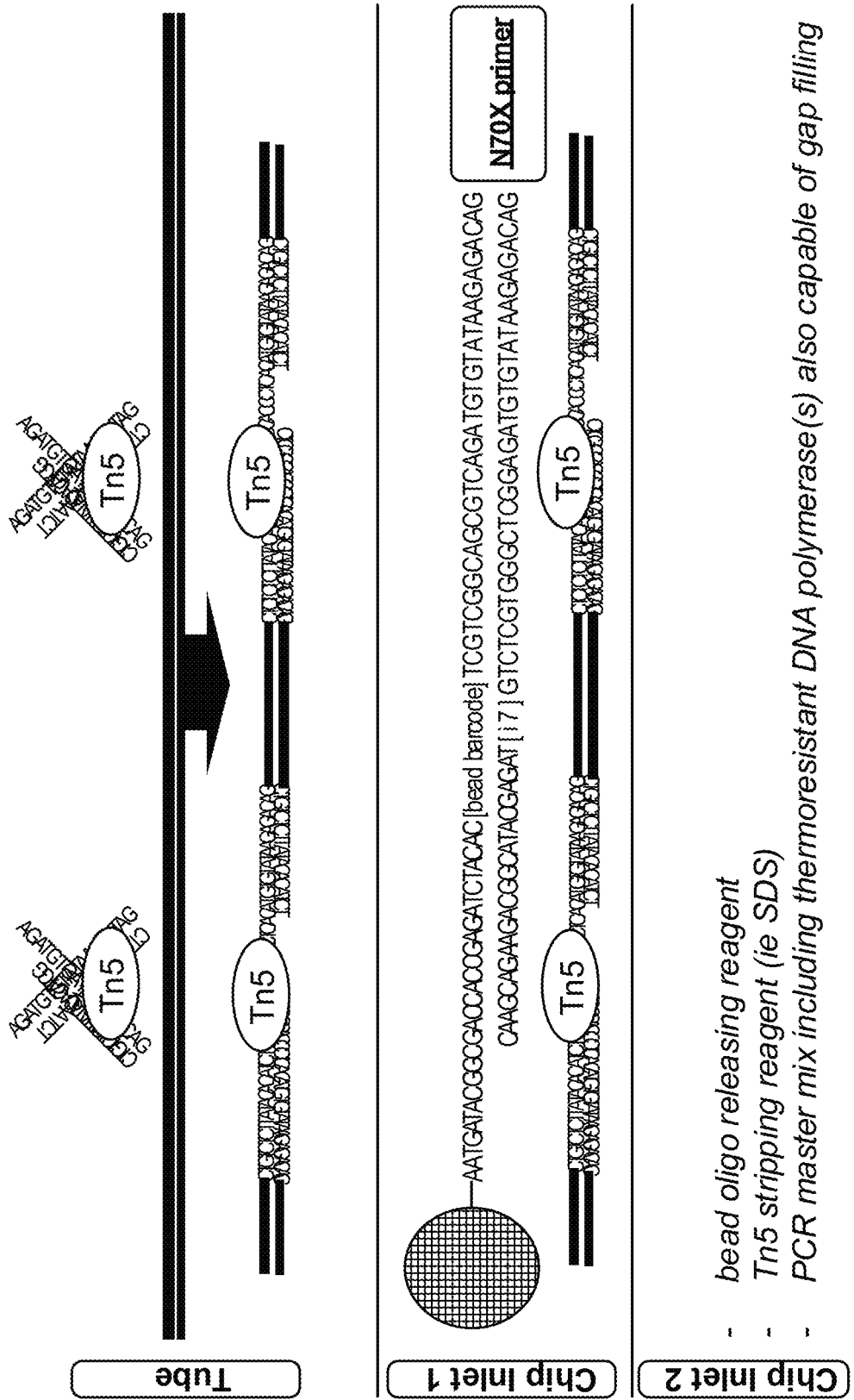

FIG. 26 is a continuation of FIG. 25 and depicts how the primers can be used. (Sequences: Tn5 adapters (SEQ ID NOS:52 and 20), Inlet 1 bead with grafting (SEQ ID NO:24) and adapter (SEQ ID NO:19), and primer (SEQ ID NO:53)).

Figure 27:

FIG. 27 is a continuation of FIG. 26. (Sequences: Terminal side of Drops (grafting (SEQ ID NO:24) and adapter (SEQ ID NO:17) and carboxyl-side of Drops (with P7/[i7] primer SEQ ID NO:34)).

Figure 28:
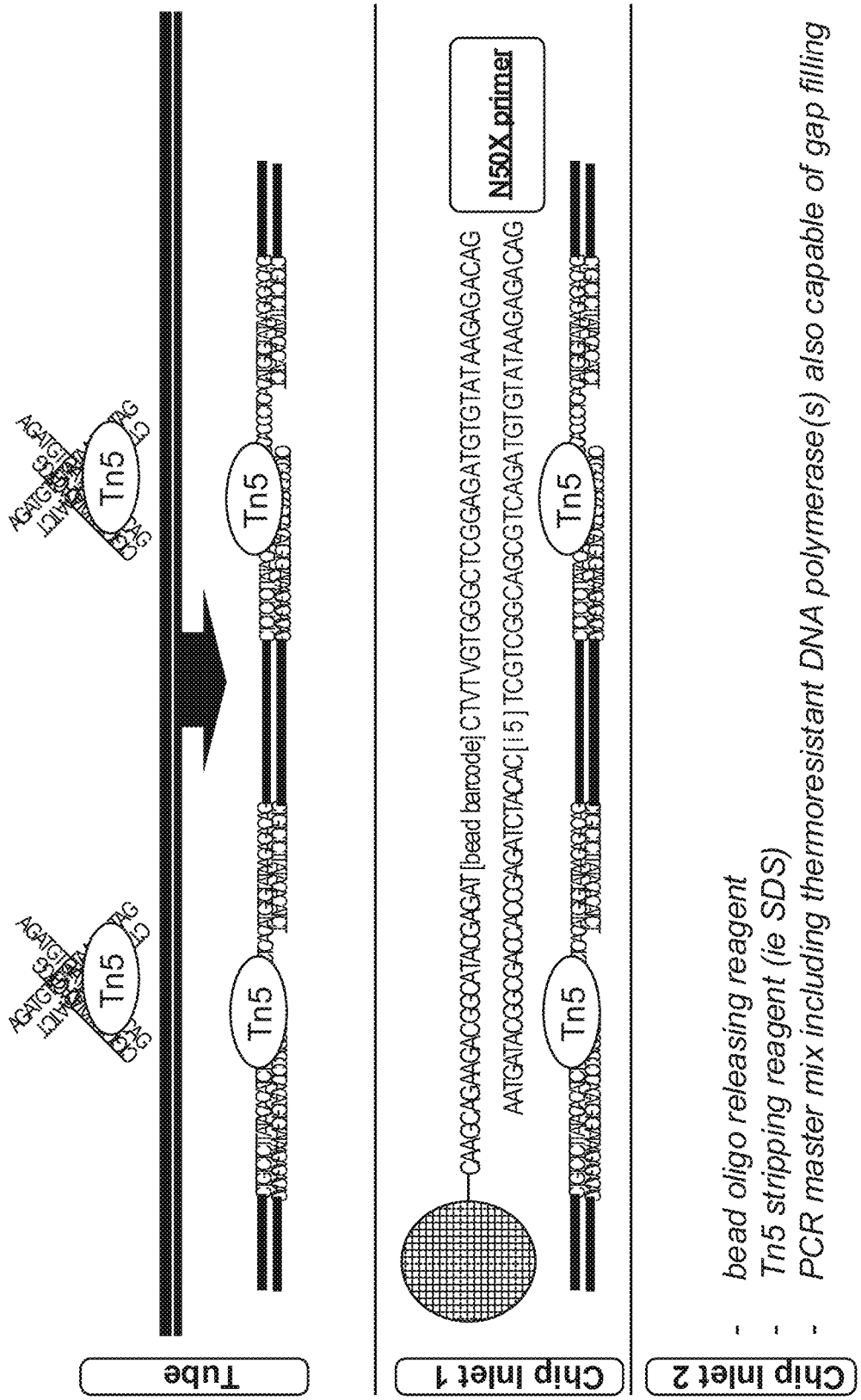

FIG. 28 is a continuation of FIG. 25 and depicts an alternative for how the primers can be used. (Sequences: Tn5 adapters (SEQ ID NOS:52 and 20), Inlet 1 bead with grafting (SEQ ID NO:27) and adapter (SEQ ID NO:21), and primer (SEQ ID NO:35)).

Figure 29:
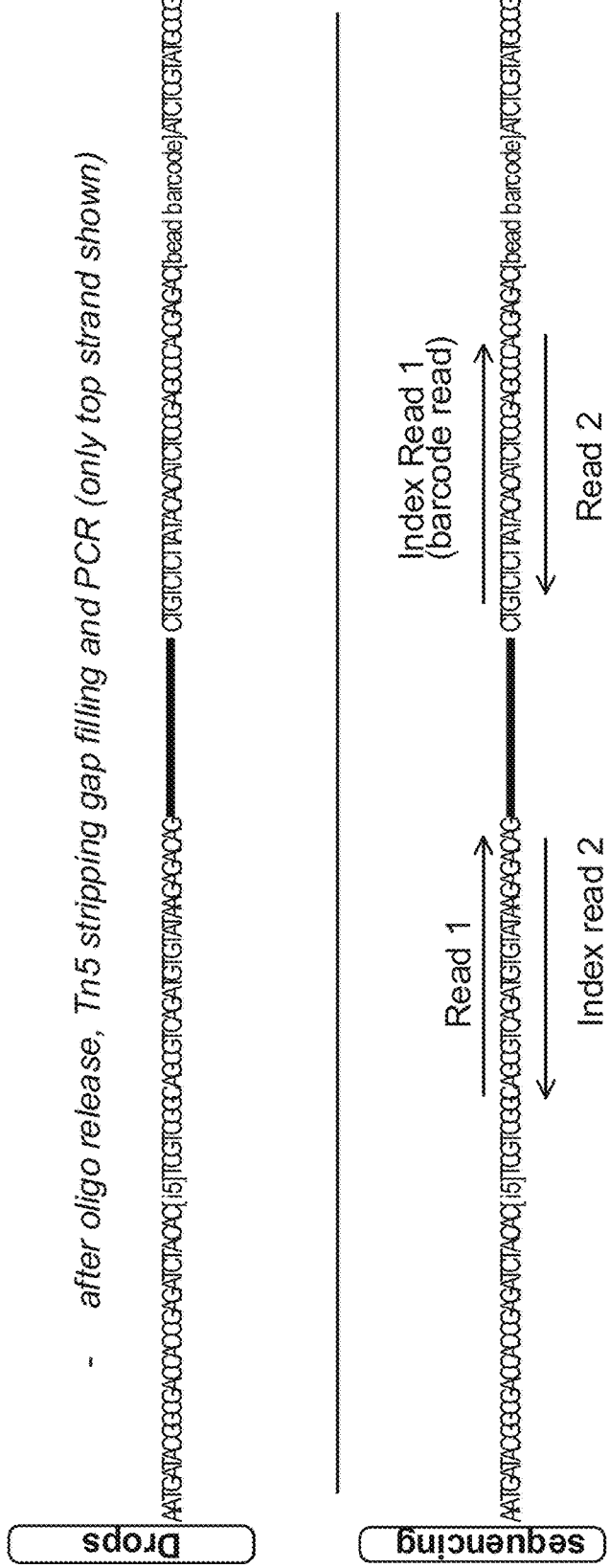

FIG. 29 is a continuation of FIG. 28. (Sequences: Terminal side of Drops (primer (SEQ ID NO:35) and carboxyl-side of drops with grafting (SEQ ID NO:30) and adapter (SEQ ID NO:36)).

Figure 30A:
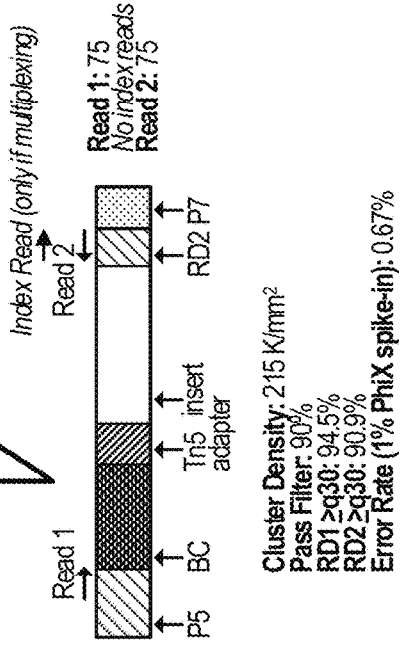
Figure 30C:
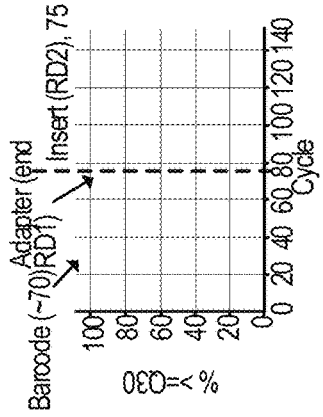
Figure 30B:
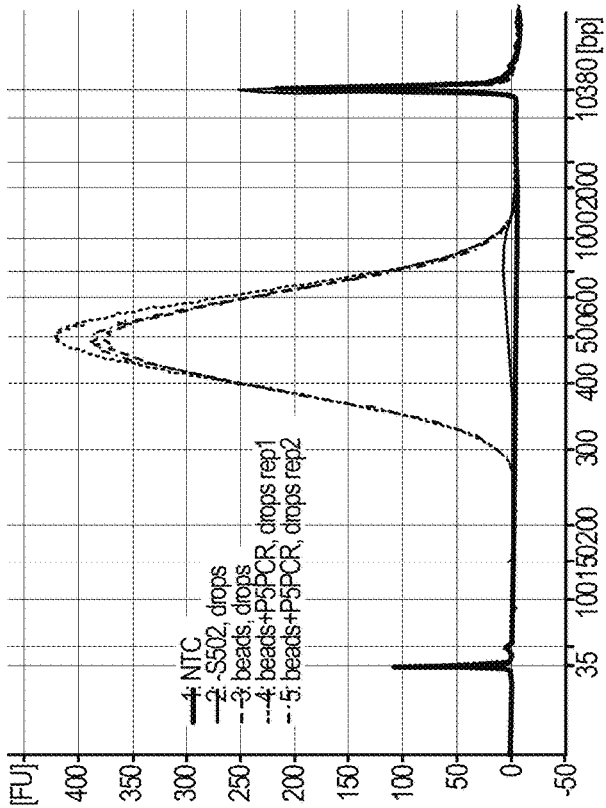

FIG. 30A-C: Experiment demonstrating CPTseq in droplets. FIG. 30A depicts the workflow. FIG. 30B depicts accumulation of product. FIG. 30C depicts a cartoon sequencing read and QC results.

FIG. 31: Expected whole genome analysis and phasing data from the data sets produced by the sequencing run shown in FIG. 30A-C.

Figure 32:
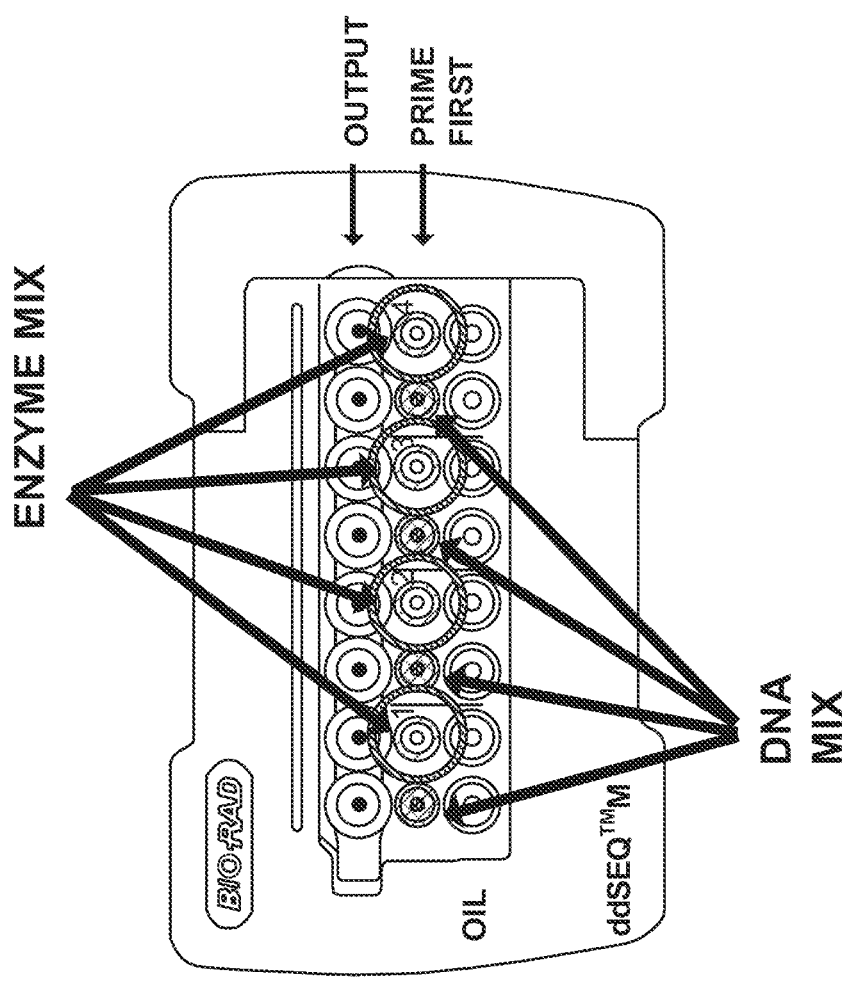

FIG. 32: Illustration of a ddSEQ chip or cartridge with indications of where to pipette the DNA and enzyme mix. The oil is pipetted in the row2 on the bottom. The DNA and enzyme mix inlets are primed first as indicated. The output wells where the emulsion results is indicated in the top row.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification. In an exemplary embodiment, amplifying refers to PCR amplification using a first and a second amplification primer.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga* maritime, or modified versions thereof. Additional examples of commercially available polymerase enzymes include, but are not limited to: Klenow fragment (New England Biolabs® Inc.), Taq DNA polymerase (QIAGEN), 9° N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein a "barcode" is a short nucleotide sequence (e.g., at least about 4, 6, 8, 10, or 12, nucleotides long) that identifies a molecule to which it is conjugated. Barcodes can be used, e.g., to identify molecules in a partition. Such a partition-specific barcode should be unique for that partition as compared to barcodes present in other partitions. For example, partitions containing target RNA from single-cells can subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some cases, the cellular barcode is provided by a "particle barcode" that is present on oligonucleotides conjugated to a particle, wherein the particle barcode is shared by (e.g., identical or substantially identical amongst) all, or substantially all, of the oligonucleotides conjugated to that particle. Thus, cellular and particle barcodes can be present in a partition, attached to a particle, or bound to cellular nucleic acid as multiple copies of the same barcode sequence. Cellular or particle barcodes of the same sequence can be identified as deriving from the same cell, partition, or particle. Such partition-specific, cellular, or particle barcodes can be generated using a variety of methods, which methods result in the barcode conjugated to or incorporated into a solid or hydrogel support (e.g., a solid bead or particle or hydrogel bead or particle). In some cases, the partition-specific, cellular, or particle barcode is generated using a split and mix (also referred to as split and pool) synthetic scheme as described herein. A partition-specific barcode can be a cellular barcode and/or a particle barcode. Similarly, a cellular barcode can be a partition specific barcode and/or a particle barcode. Additionally, a particle barcode can be a cellular barcode and/or a partition-specific barcode.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached to both strands either through barcoded primers for both first and second strand synthesis, through ligation, or in a tagmentation reaction.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N−1 deletions or other mutations from the canonical barcode sequence. Thus, barcodes that are referred to as "identical" or "substantially identical" copies refer to barcodes that differ due to one or more errors in, e.g., synthesis, polymerization, or purification errors, and thus contain various N−1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from all other barcodes of a population or different from barcodes of a different partition, cell, or bead). However, such minor variations from theoretically ideal barcodes do not interfere with the high-throughput sequencing analysis methods, compositions, and kits described herein. Therefore, as used herein, the term "unique" in the context of a particle, cellular, partition-specific, or molecular barcode encompasses various inadvertent N−1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010). Further methods and compositions for using barcode technology include those described in U.S. 2016/0060621.

A "transposase" or "tagmentase" means an enzyme that is capable of forming a functional complex with a transposon end-containing composition and catalyzing insertion or transposition of the transposon end-containing composition into the double-stranded target DNA with which it is incubated in an in vitro transposition reaction.

The term "transposon end" means a double-stranded DNA that exhibits only the nucleotide sequences (the "transposon end sequences") that are necessary to form the complex with the transposase that is functional in an in vitro transposition reaction. A transposon end forms a "complex" or a "synaptic complex" or a "transposome complex" or a "transposome composition with a transposase or integrase that recognizes and binds to the transposon end, and which complex is capable of inserting or transposing the transposon end into target DNA with which it is incubated in an in vitro transposition reaction. A transposon end exhibits two complementary sequences consisting of a "transferred transposon end sequence" or "transferred strand" and a "non-transferred transposon end sequence," or "non transferred strand" For example, one transposon end that forms a complex with a hyperactive Tn5 transposase (e.g., EZ-Tn5™ Transposase, EPICENTRE Biotechnologies, Madison, Wis., USA) that is active in an in vitro transposition reaction comprises a transferred strand that exhibits a "transferred transposon end sequence" as follows:

```
                                        (SEQ ID NO: 52)
5' AGATGTGTATAAGAGACAG 3'
``` and a non-transferred strand that exhibits a "non-transferred transposon end sequence" as follows:

```
                                        (SEQ ID NO: 20)
5' CTGTCTCTTATACACATCT 3'.
```

The 3'-end of a transferred strand is joined or transferred to target DNA in an in vitro transposition reaction. The non-transferred strand, which exhibits a transposon end sequence that is complementary to the transferred transposon end sequence, is not joined or transferred to the target DNA in an in vitro transposition reaction.

In some embodiments, the transferred strand and non-transferred strand are covalently joined. For example, in some embodiments, the transferred and non-transferred strand sequences are provided on a single oligonucleotide, e.g., in a hairpin configuration. As such, although the free end of the non-transferred strand is not joined to the target DNA directly by the transposition reaction, the non-transferred strand becomes attached to the DNA fragment indirectly, because the non-transferred strand is linked to the transferred strand by the loop of the hairpin structure.

DETAILED DESCRIPTION OF THE INVENTION

Introduction

The inventors have discovered an efficient method for maintaining contiguity of sequences such that sequences on the same haplotype can be determined and associated with each other. For example, genomic DNA can be treated with adaptor-loaded tagmentase such that the tagmentase randomly creates breakpoints in the DNA and inserts a first adaptor and a second adaptor on either side of the breakpoint. The adaptors when loaded onto a tagmentase have a common double-stranded portion and optionally a specific portion that is single-stranded and that can be the same in the case of homoadaptors or different in the case of heteroadaptors. Single-stranded adaptors are introduced to breakpoints by the tagmentase, wherein the single-stranded adaptor include the common sequence and, if present, the specific portion. The introduced adaptor sequences will have a 5' single-stranded overhang that can be filled by a polymerase. Conditions are selected such that the tagmentase does not release from the DNA, and thus forms a bridge linking DNA segments that have the same relationship (haplotype) as occurred in the genomic DNA. Thus the tagmentase step can occur in bulk (before partitions are formed). The resulting tagmentase-bridged DNA segments can be added to partitions such that one set of bridged DNA segments (e.g., on average) are in partitions. Contiguity is therefore maintained until the bridged segments have been separated into different partitions. Once in partitions, the contiguous DNA segments can be barcoded with a partition-specific barcode, thereby allowing for later identification of contiguous DNA after sequencing in bulk (after partitions contents are merged).

The partitions will further include an agent that separates the DNA segments. In embodiments in which the tagmentase itself bridges the DNA segments, an agent can be included in the partitions that disassociates the tagmentase from the DNA segments. In embodiments in which there is a linking sequence linking the tagmentase-added adaptors, an agent can be included in partitions that cleaves the linking sequence.

The partitions will further include a bead linked to a first oligonucleotide having a free 3' end. The oligonucleotide will include a barcode specific for the particular bead to which it is linked, and also includes a 3' end sequence that is specific for and complementary to an adaptor sequence on the DNA segment. The partitions can in some embodiments further include a second oligonucleotide that functions as a reverse primer, having a 3' end specific for and complementary to the adaptor sequence on the opposite end of the DNA segment compared to the adaptor at which the first oligonucleotide hybridizes.

Prior to amplification, there is a gap filling reaction such that the complement to the 5' overhang of the transposase adapter is synthesized. Gap filling does not involve ligation. Amplification is performed in the partitions. Thus, each partition only contains contiguous DNA from the genomic DNA. The resulting amplicons will contain the bead-specific barcode.

After amplification, the contents of the partitions can be merged to form a mixture of amplicons. The resulting mixture of amplicons can be nucleotide sequenced by any method desired by the user. DNA from the same haplotype will be readily identifiable as having the same bead-specific barcode.

Performing the method in partitions (e.g., droplets) allows for: 1) release of bead oligonucleotides, which makes the thermodynamics of finding binding partners more favorable and 2) performing an overhang+gap fill to create a contiguous bottom strand that is an extendible template for the released oligonucleotide primers. This also adds to efficiency multiple fold over ligation. This achieves much higher efficiency than methods performed on beads, thus better coverage, and thus fewer numbers of bead-reactions required.

Genomic DNA

Any genomic DNA can be used in the methods. In some embodiments, the DNA is from a single cell or is from a single type of cell from an organism. In some embodiments, the genomic DNA is from a eukaryote, for example from a mammal, e.g. a human. In some embodiments, the DNA is from a plant or fungus. In some embodiments, the starting DNA is purified as desired and used directly in the method. Alternatively, DNA can be treated to generate DNA fragments of a desired average size, for example using size-selection columns or gel purification. For example, in some embodiments, the starting DNA fragments are on average between 5 kb-10 Mb.

Tagmentase

Heteroadapter-loaded tagmentases and homoadapter-loaded tagmentases can be used as described herein. Homoadapter-loaded tagmentases are tagmentases that contain adaptors of only one sequence, which adaptor is added to either end of a tagmentase-induced breakpoint in the genomic DNA. Heteroadapter loaded tagmentases are tagmentases that contain two different adaptors, such that a different adaptor sequence is added to the two DNA ends created by a tagmentase-induced breakpoint in the DNA. Adapter loaded tagmentases are further described, e.g., in U.S. Patent Publication Nos: 2010/0120098; 2012/0301925; and 2015/0291942 and U.S. Pat. Nos. 5,965,443; 6,437,109; 7,083,980; 9,005,935; and 9,238,671, the contents of each of which are hereby incorporated by reference in the entirety for all purposes.

A tagmentase is an enzyme that is capable of forming a functional complex with a transposon end-containing composition and catalyzing insertion or transposition of the transposon end-containing composition into the double-stranded target DNA with which it is incubated in an in vitro transposition reaction. Exemplary transposases include but are not limited to modified TN5 transposases that are hyperactive compared to wildtype TN5, for example can have one or more mutations selected from E54K, M56A, or L372P. Wild-type Tn5 transposon is a composite transposon in which two near-identical insertion sequences (IS50L and IS50R) are flanking three antibiotic resistance genes (Reznikoff W S. *Annu Rev Genet* 42: 269-286 (2008)). Each IS50 contains two inverted 19-bp end sequences (ESs), an outside end (OE) and an inside end (IE). However, wild-type ESs have a relatively low activity and were replaced in vitro by hyperactive mosaic end (ME) sequences. A complex of the transposase with the 19-bp ME is thus all that is necessary for transposition to occur, provided that the intervening DNA is long enough to bring two of these sequences close together to form an active Tn5 transposase homodimer (Reznikoff W S., *Mol Microbiol* 47: 1199-1206 (2003)). Transposition is a very infrequent event in vivo, and hyperactive mutants were historically derived by introducing three missense mutations in the 476 residues of the Tn5 protein (E54K, M56A, L372P), which is encoded by IS50R (Goryshin I Y, Reznikoff W S. 1998. *J Biol Chem* 273: 7367-7374 (1998)). Transposition works through a "cut-and-paste" mechanism, where the Tn5 excises itself from the donor DNA and inserts into a target sequence, creating a 9-bp duplication of the target (Schaller H. *Cold Spring Harb Symp Quant Biol* 43: 401-408 (1979); Reznikoff W S., *Annu Rev Genet* 42: 269-286 (2008)). In current commercial solutions (Nextera™ DNA kits, Illumina), free synthetic ME adaptors are end-joined to the 5'-end of the target DNA by the transposase (tagmentase). In some embodiments, the tagmentase is linked to a solid support (e.g., a bead that is different from the bead linked to the forward primer). An example commercial bead-linked tagmentase is Nextera™ DNA Flex (Illumina).

In some embodiments, the adaptor(s) is at least 19 nucleotides in length, e.g., 19-100 nucleotides. In some embodiments, the adapters are double stranded with a 5' end overhang, wherein the 5' overhand sequence is different between heteroadaptors, while the double stranded portion (typically 19 bp) is the same. In some embodiments, an adaptor comprises TCGTCGGCAGCGTC (SEQ ID NO:25) or GTCTCGTGGGCTCGG (SEQ ID NO:28). In some embodiments involving the heteroadaptor-loaded tagmentase, the tagmentase is loaded with a first adaptor comprising TCGTCGGCAGCGTC (SEQ ID NO:25) and a second adaptor comprising GTCTCGTGGGCTCGG (SEQ ID NO:28). In some embodiments, the adapter comprises AGATGTGTATAAGAGACAG (SEQ ID NO:52) and the complement thereof (this is the mosaic end and this is the only specifically required cis active sequence for Tn5 transposition). In some embodiments, the adapter comprises TCGTCGGCAGCGTCAGATGTGTATAAGAGACAG (SEQ ID NO:19) with the complement for AGATGTGTATAAGAGACAG (SEQ ID NO:52) or GTCTCGTGGGCTCGGAGATGTGTATAAGAGACAG (SEQ ID NO:21) with the complement for AGATGTGTATAAGAGACAG (SEQ ID NO:52). In some embodiments involving the heteroadaptor-loaded tagmentase, the tagmentase is loaded with a first adaptor comprising TCGTCGGCAGCGTCAGATGTGTATAAGA-GACAG (SEQ ID NO:19) with the complement for AGATGTGTATAAGAGACAG (SEQ ID NO:52) and GTCTCGTGGGCTCGGAGATGTGTATAAGAGACAG (SEQ ID NO:21) with the complement for AGATGTGTATAAGAGACAG. (SEQ ID NO: 52).

In some embodiments, the adaptors have a 19 bp double stranded region and a 5' 15 bp single stranded overhang. The sequence of the 15 bp is different between heteroadaptors whereas the double-stranded region has a common sequence between adaptors (homo or heteroadaptors). See, e.g., FIG. 5.

In some embodiments, whether the tagmentase is loaded with hetero or homo adaptors, the pair of adaptors can be linked via a linking nucleotide sequence. This aspect is depicted in FIG. 21-22. The linking sequence can be any nucleotide sequence linking the two adaptors. The linking sequence can be, in some embodiments, between 2 nucleotides to 5 kb long. In some embodiments, the linking sequence can contain one or more restriction recognition sequence such that the linking sequence can be cleaved later by a restriction enzyme added to the partitions. To avoid cleavage within the DNA segments themselves, it can be beneficial to select a rare cutting restriction enzyme, for example a restriction enzyme having a recognition sequence having 8 or more nucleotides.

In other embodiments, the linking sequence can contain one or more (e.g., 2, 3, 4, 5, 6, 7, 8, 9, or 10) uracils. The linking sequence can subsequently be cleaved in the presence of uracil-DNA N-glycosylase (e.g., "UNG"), which can be included in the partition.

In other embodiments, the linking sequence can contain one or more (e.g., 2, 3, 4, 5, 6, 7, 8, 9, or 10) ribonucleotides. The linking sequence can subsequently be cleaved in the presence of base or RNase, which can be included in the partition.

Conditions for tagmentation are selected such that the tagmentase creates breakpoints in the DNA and such that adaptors loaded on the tagmentase are added to either end of the breakpoint. The tagmentase introduces a single-stranded adaptor sequence on either end of the breakpoint, forming a 5' overhang. The 5' overhang is then filled ("gap filled") by a polymerase to create a double-stranded sequence at either end of the DNA segments. See, e.g., FIG. 9. The non-transferred bottom strand is thus rendered contiguous and complementary to the transferred top strand. This contiguous bottom strand is now compatible with polymerase extension reactions, e.g., PCR. Thus "gap filling" is the process after tagmentation that renders the bottom strand (the one that is not transferred) contiguous with the top strand at the end of the DNA segments. Gap filling refers to reconstitution of the bottom strand. This is done preferentially by a DNA polymerase that extends back from the 3' of the bottom non-transferred strand that is upstream of the gap. The polymerase that gap fills can either have 5' to 3' exo activity or strand displacing activity to help overcome the non-transferred mosaic end. Neither gap filling nor adding of the barcode involves ligation.

Conditions are also selected such that the tagmentase remains bound to the DNA breakpoints thereby maintaining contiguity. Tagmentase has been observed to remain bound to DNA until a detergent such as SDS is added to the reaction (Amini et al. *Nature Genetics* 46(12):1343-1349).

Partitions

Any type of partition can be used in the methods described herein. While the method has been exemplified using droplets it should be understood that other types of partitions can also be used.

In some embodiments, prior to contact to the segmented DNA, the partitions will contain a first oligonucleotide linked to a bead and optionally a second reverse oligonucleotide primer. The partitions can also include a sufficient amount of an agent to remove tagmentase from the DNA or to cleave the linking sequences, if present. As described herein, subsequently, the segmented and linked DNA can be added to partitions. The number of segmented and linked DNA molecules, while ideally in some embodiments, can be one per partition, can be selected as needed depending for example on the number of partitions and other factors.

Methods and compositions for partitioning are described, for example, in published patent applications WO 2010/036, 352, US 2010/0173,394, US 2011/0092,373, and US 2011/0092,376, the contents of each of which are incorporated herein by reference in the entirety. The plurality of mixture partitions can be in a plurality of emulsion droplets, or a plurality of microwells, etc.

In some embodiments, the primers and other reagents can be partitioned into a plurality of mixture partitions, and then linked DNA segments can be introduced into the plurality of mixture partitions. Methods and compositions for delivering reagents to one or more mixture partitions include microfluidic methods as known in the art; droplet or microcapsule merging, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the mixture partitions can be picowells, nanowells, or microwells. The mixture partitions can be pico-, nano-, or micro-reaction chambers, such as pico, nano, or microcapsules. The mixture partitions can be pico-, nano-, or micro-channels. The mixture partitions can be droplets, e.g., emulsion droplets.

In some embodiments, the partitions are droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample or reagents.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7° 8°, 9° 10°, 15°, 20°, 25°, 30°, 35° or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000,000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

As noted above, the partitions will include one or a few (e.g., 1, 2, 3, 4) beads per partition, where in each bead is linked to a first oligonucleotide primer having a free 3' end. The first oligonucleotide primer will have a bead-specific barcode and a 3' end that is complementary to an adaptor. In some embodiments, the barcode will be, e.g., 2-10 nucleotides in length, e.g., 2, 3, 4, 5, 6, 7, 8, 9, or 10 nucleotides. The barcode can be continuous or discontinuous, i.e., broken up by other nucleotides. In some embodiments, the 3' end will be complementary to the entire adaptor sequence. In some embodiments, at least the 3'-most 6, 7, 8, 9, 10, 11, 12, 13, 14, 15, 16, 17, 18, 19, or 20 of the oligonucleotide are complementary to a sequence in the adaptor. In some embodiments, the first oligonucleotide primer further comprises a universal or other additional sequence to assist with downstream manipulation or sequencing of the amplicon. For example, when Illumina-based sequencing is used the first oligonucleotide primer can have a 5' P5 or P7 sequence (optionally with the second oligonucleotide primer having the other of the two sequences). Optionally, the first oligonucleotide primer comprises a restriction or cleavage site to remove the first oligonucleotide primer from the bead when desired. In some embodiments, once the DNA segments are in the partitions with the bead-linked first oligonucleotide primer, the first oligonucleotide primer is cleaved from the bead prior to amplification.

The term "bead" refers to any solid support that can be in a partition, e.g., a small particle or other solid support. Exemplary beads can include hydrogel beads. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240.

Methods of linking oligonucleotides to beads are described in, e.g., WO 2015/200541. In some embodiments, the oligonucleotide configured to link the hydrogel to the barcode is covalently linked to the hydrogel. Numerous methods for covalently linking an oligonucleotide to one or more hydrogel matrices are known in the art. As but one example, aldehyde derivatized agarose can be covalently linked to a 5'-amine group of a synthetic oligonucleotide.

As noted elsewhere herein, the partitions can also contain a second oligonucleotide primer, which can optionally be linked to the bead, or not. This primer can function as a reverse primer for the first oligonucleotide primer such that the two oligonucleotides generate an amplicon in PCR. The second oligonucleotide primer will have a 3' end that is complementary to an adaptor sequence, i.e., the adaptor sequence at the opposite end of the DNA segment compared to the adaptor sequence targeted by the first oligonucleotide primer. In some embodiments, the 3' end will be complementary to the entire adaptor sequence. In some embodiments, at least the 3'-most 6, 7, 8, 9, 10, 11, 12, 13, 14, 15, 16, 17, 18, 19, or 20 of the oligonucleotide are complementary to a sequence in the adaptor. The second oligonucleotide primer can also contain a universal or other additional sequence to assist with downstream manipulation or sequencing of the amplicon. For example, when Illumina-based sequencing is used the second oligonucleotide primer can have a 5' P5 or P7 sequence for binding to the Illumina flow cell (optionally with the first oligonucleotide primer having the other of the two sequences).

The partitions can also contain an agent that removes tagmentase from the DNA segments. In some embodiments, the agent is a detergent, e.g., an ionic or non-ionic detergent. An exemplary detergent is sodium dodecyl sulfate (SDS). For example, the inventors have determined that concentrations of 0.1 and 0.2% SDS are sufficient to remove the tagmentase and yet are sufficiently low to not interfere with amplification. Thus, in some embodiments, the partitions contain 0.02-0.4%, e.g., 0.05-0.3% SDS. In some embodiments (e.g., in which droplets are used) the agent is compatible with droplet formation. In some embodiments, the agent is a polymerase, e.g., the polymerase used for gap filling or that is otherwise used to amplify the DNA. Alternatively, in some embodiments, the tagmentase can be displaced by heat. For example, in some embodiments, heating to 70 C degrees or more (e.g., around 72° C.) reduces affinity of the tagmentase for the DNA or displaces the tagmentase.

Prior to amplification, one can remove or cleave the first oligonucleotide primer from the bead. This can be achieved by any method as desired. Methods of cleaving include, but are not limited to altering the pH or contacting the oligonucleotides with UDG/ApeI or a restriction endonuclease. In some embodiments, the oligonucleotide is linked to the bead via one or more uracils (Us) and USER enzyme (e.g., from NEB) is used to cleave the Us incorporated in the oligo backbone. USER has 2 enzymes: UDG and Endonuclease VIII. In some cases, the oligonucleotides are attached to a solid support through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol, dithiothreitol (DTT), or tris(2-carboxyethyl)phosphine (TCEP). It can be advantageous to release the first oligonucleotide primer from the bead for a number of reasons. For example, thermodynamics of DNA interactions will greatly increase.

Amplification can be achieved within the partitions (before combining the contents to the partitions). Various digital amplification method are known and can be used.

Following amplification, the contents of the partitions are combined and sequenced. Any method of nucleotide sequencing can be used as desired so long as at least some of the DNA segments sequence and the barcode sequence is determined. Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511, 803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., Clinical Chem., 55. 641-658, 2009; MacLean et al., Nature Rev. Microbial, 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

Upon competition of sequencing, sequences can be sorted by same barcode, wherein sequences having the same barcode came from the same partition and thus are contiguous. In some embodiments, sequences linked based on common barcode sequence can be determined and optionally SNPs can be detected per fragment per barcode. In some embodiments, one can detect fragment colocalization to a single barcode greater than chance (skewed distributions), thereby detecting a rearrangement.

Example

The following examples are offered to illustrate, but not to limit, the claimed invention.

An experiment demonstrating CPTseq in droplets was performed. The workflow provided in FIG. 30A covered 5 conditions tested for the DNA aqueous inlet: (1) Beads, (2-3) beads+P5 PCR primer (×2 replicates), (4) N70X only, and (5) no template control (NTC). The method protocol is provided below. Briefly, the DNA was tagmented (with Tagment DNA enzyme (TDE)) in a tube to generate CPT DNA, five emulsions made using that CPT DNA, PCR reagents and a variety of oligos that vary per condition. In the droplet, the oligos were released from the beads for the bead conditions, the Tn5 displaced from the CPTDNA, the gaps filled and PCR performed for 10 cycles. The droplets were then broken, the DNA purified, and a second nested PCR was performed followed by a final purification. The products were run on a gel and results are illustrated in FIG. 30B. The test conditions using the beads are shown for conditions 1-3. The absence of amplification for the negative control in condition 4 omitting the bead and all bead primers, but including the N70X primer, argues that the amplification in conditions 1-3 is bead dependent. The NTC showing no amplification was confirmed for condition 5. Sequencing methods on Illumina sequencers for the bead sample is shown in FIG. 30C together with the sequencing QC metrics. High cluster densities and the majority of bases with Q scores of greater than 30 argue that sequencing was successfully executed.

FIG. 31 shows expected whole genome analysis and phasing data from the data sets produced by the sequencing run shown in FIG. 30A-C, in the CPTseq in droplets expected results. Beads in bulk data (Zhang et al 2017 *Nature Biotechnology*) and 10× data (Zheng et al 2017 *Nature Biotechnology*) are provided for comparison.

Detailed Protocol:
Equipment: Thermocycler (either C1000 touch or T100)
Tagment reaction (150 haploid genomes/uL)

|  | | | | 100 | | total volume | | |
|---|---|---|---|---|---|---|---|---|
| Component | Part number | LOT NUMBER | Supplier | stock | unit | final | unit | MM (uL) |
| TD buffer DNA, diluted in 10 mM TRIS, pH8 | | | | 2 1.25 | X ng/uL | 1 0.5 | X ng/uL | 50.0 40.0 |
| TDE Enzyme | | | | 10 | U/uL | 1 | U/uL | 10.0 |
| Total | | | | | | | | 100.0 |

Tagment Reaction
  Mix thoroughly by pipetting.
  Incubate in a thermocycler (Lid temperature: 55 C, Sample Volume: 100 uL). 55° C. 10 minutes
4° C.
  Keep on ice. At this concentration of DNA, 150 haploid genomes/uL (for use in enzyme mix).
  Oligos P5-short
                                              (SEQ ID NO: 54)
AATGATACGGCGAC P7-short
                                              (SEQ ID NO: 55)
CAAGCAGAAGACGG N70X
                                              (SEQ ID NO: 56)
CAAGCAGAAGACGGCATACGAGATXXXXXXXXXGTCTCGTGGGCTCGG Enzyme Mix:

|  |  | 25 | volume per reaction | | | | | | |
|---|---|---|---|---|---|---|---|---|---|
|  |  | 8 | total reactions | | | | | | |
| Component | Part number | Supplier | stock | unit | final (2x) | unit | for 1 rxn | MM |
| Water | AM9937 | Ambion | N/A | N/A | N/A | N/A | 8.94 | 71.53 |
| Drop Solution | N/A | Bio-Rad | 15 | x | 1 | x | 1.67 | 13.33 |
| Optiprep | D1556 | Sigma | 100 | % | 3 | % | 0.75 | 6.00 |
| USER | M5505 | NEB | 1 | U/uL | 0.125 | U/uL | 3.13 | 25.00 |
| DTT | N/A | Bio-Rad | 300 | mM | 10 | mM | 0.83 | 6.67 |
| HS Q5 Enzyme, concentrated | custom | NEB | 10 | U/uL | 0.04 | U/uL | 0.10 | 0.80 |
| HS Q5 Enzyme | M0491L | NEB | 2 | U/uL | 0.02 | U/uL | 0.25 | 2.00 |
| KOD Xtreme Hot Start DNA Pol | 71975 | Millipore/Sigma | 1 | U/uL | 0.04 | U/uL | 1.00 | 8.00 |
| DNA | | | 150 | hap genomes/ uL | 50 | hap genomes/ uL | 8.33 | 66.67 |
| Total | | | | | | | 25.00 | 200.00 |

DNA Mix

| Component | Part number | Supplier | stock | unit | final (2x) | unit | for 1 rxn | MM |
|---|---|---|---|---|---|---|---|---|
| | 25 | volume per reaction | | | | | | |
| | 8 | total reactions | | | | | | |
| Water | AM9937 | Ambion | N/A | N/A | N/A | N/A | 0.33 | 2.67 |
| Drop Solution | N/A | Bio-Rad | 15 | x | 1 | x | 1.67 | 13.33 |
| Optiprep | D1556 | Sigma | 100 | % | 28 | % | 7.00 | 56.00 |
| P5 short* | N/A | IDT | 100000 | nM | 2000 | nM | 0.50 | 4.00 |
| dNTPs | | | 10 | mM | 0.8 | mM | 2.00 | 16.00 |
| 1 step beads (Full P5 adaptered)* add 1 uL to each sample after aliquoting mastermix | N/A | Bio-Rad | 3200 | beads/uL | 1600 | beads/uL | 12.50 | 100.00 |
| N70X primer | N/A | IDT | 50000 | nM | 2000 | nM | 1.00 | 8.00 |
| Total | | | | | | | 25.00 | 200.00 |

Enzyme/DNA Mix:

Make Enzyme mix according to table above.

Make DNA mix according to table above. Do not add N70X primer if multiplexing.

After aliquoting DNA mix, add 1 uL of N70X oligo (50 uM) to each sample. Keep both DNA and Enzyme mix on ice until droplet making.

The above mixes can be modified. However, for successful drop generation, some constants are helpful.

Constants for successful drop generation:
1) Drop solution quantities
2) Optiprep concentrations
3) The amount of glycerol contained in the enzyme mixes Droplet Generation For all droplet generation and transfer steps, use Rainin pipettes and corresponding tips.

Rinse pipette tip with solution before loading chip. Depress pipette plunger only to first stop when loading cartridge to avoid bubbles Insert cartridge into cartridge holder. Check that cartridge is fully inserted and lying flat against the bottom of the holder, then close the lever.

Using a reservoir and a P20 multichannel pipette, add 20 uL of prime solution to each well of the second row of the cartridge.

Allow prime solution to remain in wells for 1 minute, then remove all solution with a multichannel pipette. Do not allow prime solution to remain in wells longer than 3 minutes.

Mix DNA solution by pipetting. Using a P20 single-channel pipette, load 20 uL into the bottom of the B ports.

Mix Enzyme solution by pipetting. Using a P20 single-channel pipette, load 20 uL into the bottom of the ports numbered 1-4. See FIG. 32.

Note: Do not leave any ports in the second row empty.

Pour EvaGreen oil into a reservoir. Using a P200 multichannel pipette, load 80 uL of oil into each well of the bottom row of the cartridge labeled OIL.

Place loaded cartridge holder in ddSEQ Single-Cell Isolator, press silver button of top of machine to close.

Once machine is finished running (all 3 indicator lights are solid green), remove cartridge holder.

Using a P50 multichannel pipette set at 43 uL with Rainin tips, gently and slowly aspirate all encapsulated sample (~40 uL) from the output wells. Transfer to a 96-well PCR plate.

PCR: Incubate in a thermocycler (Lid temperature: 105 C, Sample Volume: 50 uL).

Note: Use either Bio-Rad C1000 Touch (Deep Well) or T100 Thermal Cycler

| | |
|---|---|
| 37° C. | 30 min |
| 72° C. | 5 min |
| 98° C. | 30 sec |
| 37° C. | |
| 72° C. | 10 sec |
| 98° C. | 30 sec |
| 37° C. | 120 sec |
| 72° C. | |
| 98° C. | 5 min |
| 4° C. | |

Emulsion Breakage and Cleanup—if Pooling Chips

Add 10 uL of Droplet Disruptor to each sample (2 wells/sample)

Add 40 uL of water. Do not mix.

Add 70 uL Ampure beads (1× cleanup).

Pipette mix in the aqueous layer only until the beads are evenly distributed. Do not mix the aqueous layer with the oil layer at the bottom of the well.

After mixing, each sample should have 2 distinct layers: an oil layer at the bottom of the well and a homogenous brown aqueous layer on top.

Incubate mixture at room temperature for 5 minutes

Place on magnetic stand and wait 5 minutes.

Keeping plate on the magnetic stand, remove and discard the supernantant, including oil.

Wash 2 times on the magnet as follows:

Add 200 uL freshly prepared 80% EtOH to each well.

Incubate for 30 seconds

Remove and discard all supernatant from each well.

Using a P20 pipette, remove residual 80% EtOH from each well.

Air-dry on the magnetic stand for ~10 minutes. Dry time can vary depending on temperature/humidity of room. Do not overdry pellet.

Remove plate from the magnetic stand. Add 10 uL RSB to each sample well. Pipette to mix.

Incubate at room temperature (not on magnetic stand) for 2 minutes.

Place tube on magnetic stand, wait ~2 minutes or until solution is clear

Combine the 2 wells for each sample into a single well by transferring 10 uL of supernatant from each sample well to a new plate.

The final volume for each sample (now combined) should be 20 uL. Run 1 uL on HS DNA chip.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A plurality of partitions, the partitions comprising:
    a bead,
    a forward primer oligonucleotide cleaved from the bead, the forward primer oligonucleotide having a bead-specific barcode and a 3' end specific for and complementary to a first or second adaptor;
    a reverse primer oligonucleotide having a 3' end complementary to the first or second adaptor, wherein the forward primer 3' end and the reverse primer 3' end are complementary to different adaptors selected from the first adaptor and the second adaptor; and
    fragments of genomic DNA reacted with an adapter-loaded tagmentase such that the DNA fragments comprise breakpoints in the fragments and an inserted adaptor at the break points, wherein the tagmentase binds the breakpoints to form linked DNA segments in the form of DNA segment-first adaptor tagmentase second adaptor-(DNA segment-first adaptor tagmentase second adaptor)n-DNA segment, where n is any integer and "-" indicates a covalent linkage.

2. The plurality of partitions of claim 1, wherein the partitions are droplets in an emulsion.

3. The plurality of partitions of claim 1, wherein the partitions comprise on average 0.02-3 beads.

4. The plurality of partitions of claim 1, wherein the genomic DNA is from a single cell.

5. The plurality of partitions of claim 1, wherein the genomic DNA is from a mammal or plant.

6. The plurality of partitions of claim 1, wherein the first adaptor and the second adaptor have different sequences.

7. The plurality of partitions of claim 6, wherein the first adaptor and the second adaptor are less than 50% identical.

8. The plurality of partitions of claim 1, wherein the first adaptor and the second adaptor have identical sequences.

9. The plurality of partitions of claim 1, wherein the first adaptor and the second adaptor are linked by both the tagmentase and a linking sequence.

10. The plurality of partitions of claim 9, wherein the linking sequence comprises a restriction recognition sequence.

11. The plurality of partitions of claim 9, wherein the linking sequence comprises one or more uracils.

12. The plurality of partitions of claim 9, wherein the linking sequence comprises one or more ribonucleotide.

13. The plurality of partitions of claim 1, wherein n is an integer selected from 1-10,000.

14. The plurality of partitions of claim 1, comprising at least 10,000 different partitions.

15. The plurality of partitions of claim 10, wherein the partitions further comprise a restriction enzyme that recognizes the restriction recognition sequence.

16. The plurality of partitions of claim 11, wherein the partitions further comprise a uracil-DNA N-glycosylase.

* * * * *